(12) United States Patent
Scheller et al.

(10) Patent No.: US 9,339,415 B2
(45) Date of Patent: May 17, 2016

(54) MULTI-PLANE SURGICAL INCISION GUIDE

(75) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 492 days.

(21) Appl. No.: 13/572,349

(22) Filed: Aug. 10, 2012

(65) Prior Publication Data

US 2013/0053875 A1    Feb. 28, 2013

Related U.S. Application Data

(60) Provisional application No. 61/526,486, filed on Aug. 23, 2011.

(51) Int. Cl.
*A61B 17/3211* (2006.01)
*A61F 9/013* (2006.01)

(52) U.S. Cl.
CPC ............ *A61F 9/0133* (2013.01); *A61B 17/3211* (2013.01); *A61B 2017/32113* (2013.01)

(58) Field of Classification Search
CPC .......................... A61F 9/0133; A61B 17/3211
USPC .................................. 606/166, 170, 171, 172
See application file for complete search history.

(56) References Cited

U.S. PATENT DOCUMENTS

| | | | |
|---|---|---|---|
| 5,370,652 A * | 12/1994 | Kellan | 606/166 |
| 5,690,658 A * | 11/1997 | McAdams | 606/166 |
| 5,876,415 A | 3/1999 | Pierce et al. | |
| 6,171,324 B1 * | 1/2001 | Cote et al. | 606/166 |
| 6,220,133 B1 | 4/2001 | Gosselin | |
| 6,656,186 B2 | 12/2003 | Meckel | |
| 2006/0070186 A1 | 4/2006 | Karlstedt | |
| 2008/0215078 A1 * | 9/2008 | Bennett | 606/166 |
| 2009/0157110 A1 * | 6/2009 | Muto | A61B 17/3211 606/167 |
| 2010/0049229 A1 | 2/2010 | Archambault | |
| 2010/0228226 A1 * | 9/2010 | Nielsen | A61M 5/158 604/506 |
| 2011/0106122 A1 * | 5/2011 | Cetola | 606/167 |

* cited by examiner

*Primary Examiner* — Sarah W Aleman
*Assistant Examiner* — Socrates L Boutsikaris
(74) *Attorney, Agent, or Firm* — Kevin P. Rollins

(57) ABSTRACT

A surgical blade may include a surgical incision guide configured to guide a surgical incision. The surgical incision guide may include one or more surgical incision guide marks. A surgical incision guide mark may be configured to provide information about a surgical incision. For example, a surgeon may compare a location of a surgical incision guide with a portion of a tissue to identify an incision depth. Illustratively, a surgeon may compare a location of a surgical incision guide with a portion of a tissue to identify an optimum incision depth to adjust an orientation of a surgical blade.

20 Claims, 28 Drawing Sheets

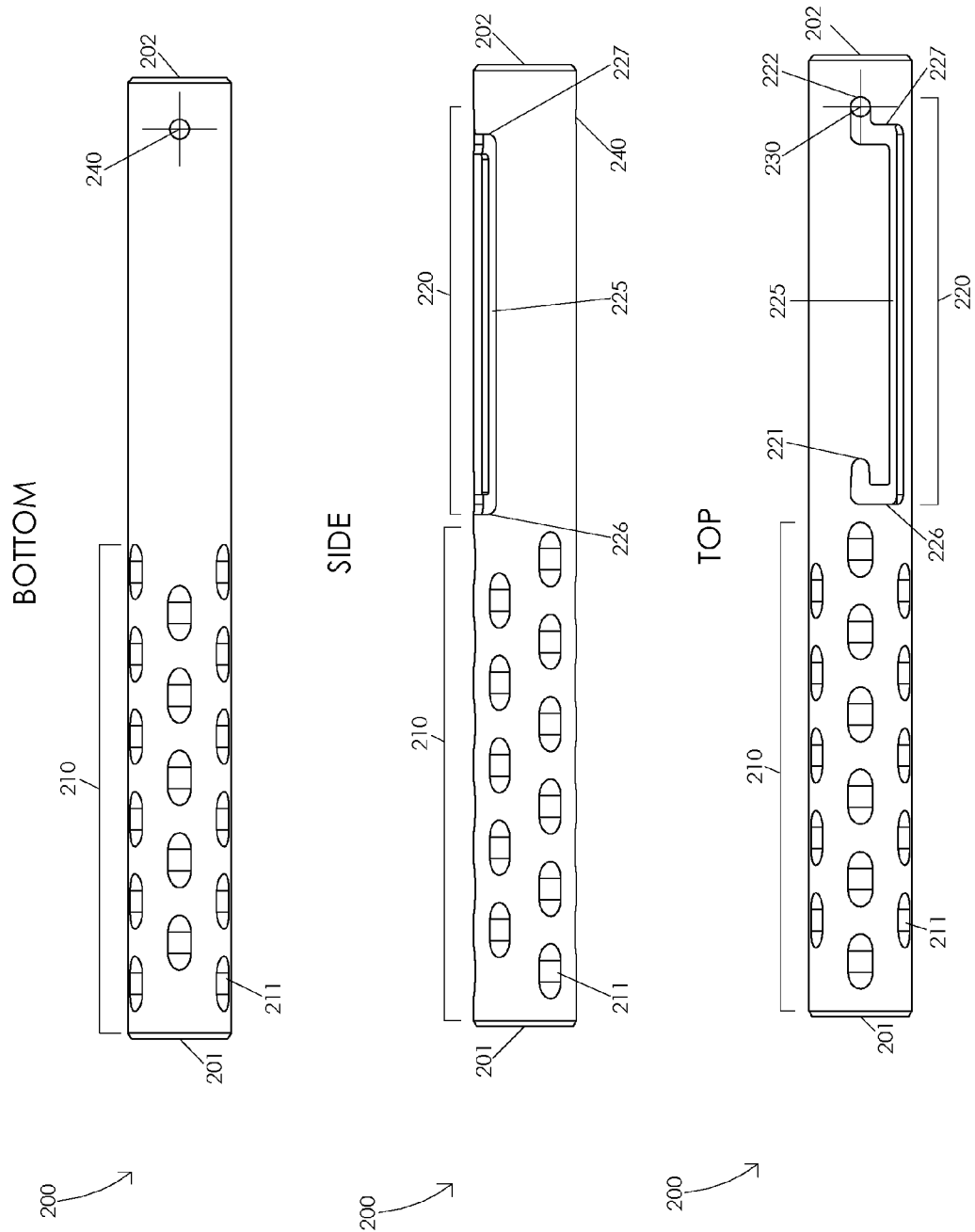

MULTI-PLANE SURGICAL INCISION GUIDE

CROSS-REFERENCE TO RELATED APPLICATIONS

This Application claims the benefit of U.S. Provisional Application No. 61/526,486, filed Aug. 23, 2011.

FIELD OF THE INVENTION

The present disclosure relates to a surgical instrument, and, more particularly, to a surgical instrument for making surgical incisions.

BACKGROUND OF THE INVENTION

Some surgical procedures require a surgical instrument with an extremely sharp blade. In order to create very precise incisions in a tissue that is difficult to cut due to, e.g., the tissue's biological composition, it is important for a surgeon to have an instrument with an extremely sharp blade. For example, eye surgeons may need to cut a patient's cornea during various surgical procedures, e.g., a common cataract surgery. If a patient's cornea is not cut with an extremely sharp blade, then the force required to make an incision in the patient's cornea with a less than extremely sharp blade may cause the corneal surface to indent before the less than extremely sharp blade pierces the patient's cornea. The corneal surface indentation creates a non-uniform surgical incision which prevents the cornea tissue from healing in a natural position. Rather, the cornea tissue heals in an aspherical position with an imprecise optical surface, e.g., resulting in a corneal astigmatism.

Unfortunately, surgical instruments with extremely sharp blades present an inherent risk of injury to professionals involved in the packaging, shipping, handling, and use of the surgical instruments for surgical procedures. Although any sharp edge may be capable of causing injury if mishandled, extremely sharp blades can cause significant trauma with very little force. If a small amount of force applied to a conventional blade against a person's tissue may cause a superficial incision in the person's tissue, then the same small amount of force applied to an extremely sharp blade against the person's tissue may be capable of inflicting a deep and serious wound. Thus, there is a need for a surgical instrument with an extremely sharp blade that minimizes the risk of injury to individuals involved in the packaging, shipping, handling, and use of the surgical instrument for surgical procedures.

Although extremely sharp blades may facilitate a surgeon's ability to create precise, uniform surgical incisions, there is still a risk that an incision performed with an extremely sharp blade may heal improperly. For example, severed edges of tissue may heal unevenly unless sutures are used to hold the severed edges in a natural position. Unfortunately, suturing delicate tissue may pose additional risks to a patient. However, a surgeon may attempt a multi-plane incision to ensure that a surgical incision heals properly. A surgeon may perform a multi-plane incision by initially penetrating a tissue to a first depth with a blade oriented at a first angle relative to the tissue and then penetrating the tissue to a second depth with the blade oriented at a second angle relative to the tissue. A successful multi-plane incision increases the total surface area of the tissue severed by a surgical blade and also creates a surgical geometry in each side of the tissue severed by the surgical blade wherein two sides of the tissue may only be reunited and heal in a single position, i.e., a natural position.

Unfortunately, multi-plane surgical incision procedures are difficult for a surgeon to perform accurately. Additionally, it is difficult for a surgeon to repeat an accurate multi-plane incision with precision. Thus, there is a need for a surgical instrument with a surgical incision guide configured to allow surgeons to perform accurate and repeatable multi-plane surgical incisions.

BRIEF SUMMARY OF THE INVENTION

The present disclosure provides a surgical instrument handle for selectively actuating a surgical blade. Illustratively, the surgical blade may comprise a surgical incision guide configured to guide a surgical incision. In one or more illustrative embodiments, a surgical instrument handle may selectively actuate a surgical blade between a safe position wherein the surgical blade is contained within an outer sleeve and an extended position wherein the surgical blade is at least partially extended from a distal end of the outer sleeve. Illustratively, a surgeon or a surgeon's assistant may receive a surgical instrument handle for selectively actuating a surgical blade in a safe position wherein the surgical blade is contained within an outer sleeve. The surgeon or the surgeon's assistant may then selectively actuate the surgical blade from the safe position to an extended position wherein the surgical blade is at least partially extended from a distal end of the outer sleeve. After completion of all or a portion of a surgical procedure, the surgeon or the surgeon's assistant may then selectively actuate the surgical blade from the extended position to the safe position.

In one or more embodiments, a surgical instrument may comprise an outer sleeve, an inner handle configured to actuate relative to the outer sleeve, a surgical blade fixed to a distal end of the inner handle, and a detent configured to selectively fix a position of the inner handle relative to the outer sleeve. Illustratively, the surgical instrument may be selectively actuated between a first position of the inner handle relative to the outer sleeve and a second position of the inner handle relative to the outer sleeve. In the first position, the surgical blade may be contained within the outer sleeve. In the second position, the surgical blade may be at least partially extended from a distal end of the outer sleeve for use in a surgical procedure. In one or more embodiments, the surgical blade may comprise a surgical incision guide configured to guide a surgical incision.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 2A, 2B, and 2C are schematic diagrams of an outer sleeve;

DETAILED DESCRIPTION OF AN ILLUSTRATIVE EMBODIMENT

Figure 1A:
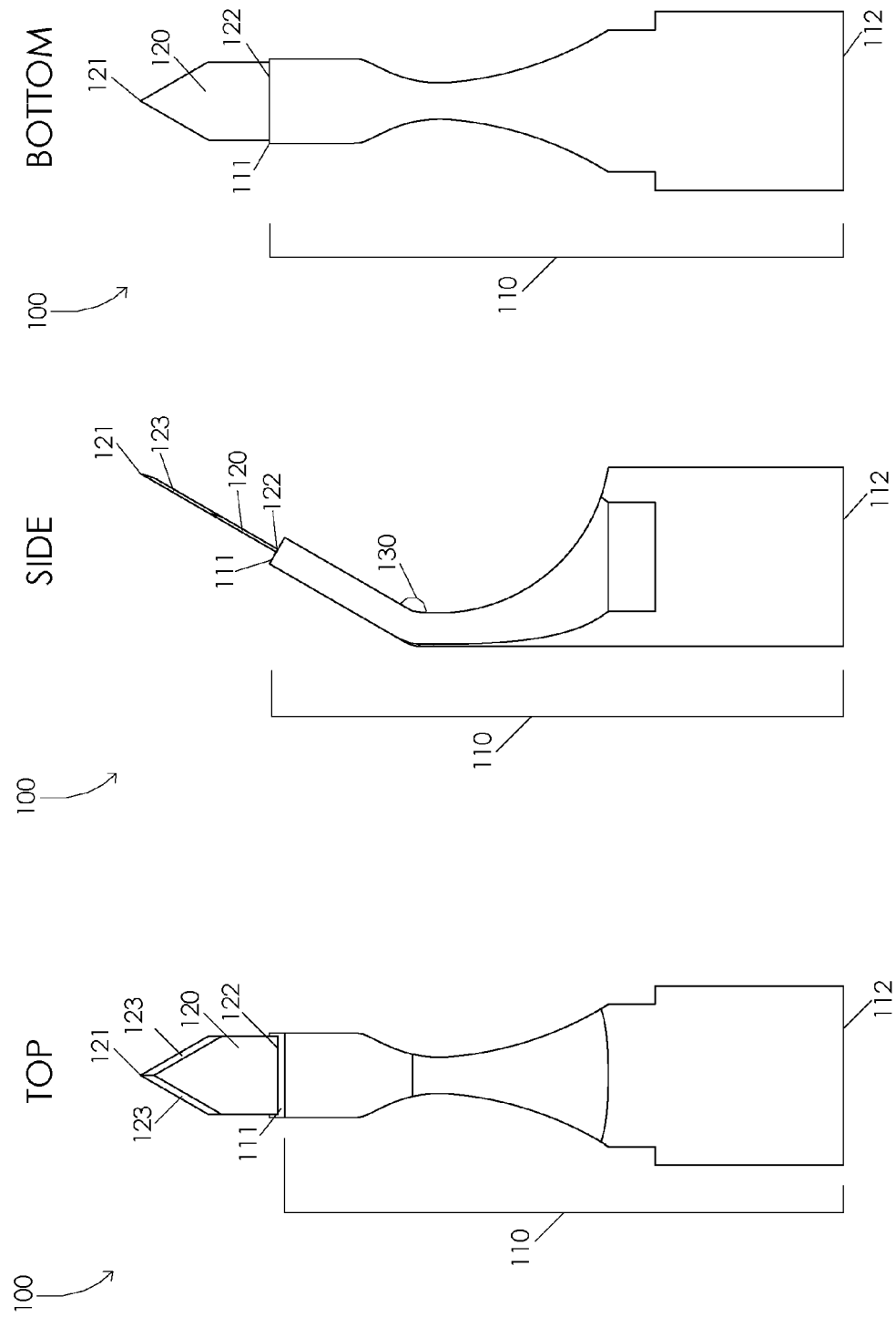
FIGS. 1A and 1B are schematic diagrams illustrating a surgical blade.
Figure 1B:
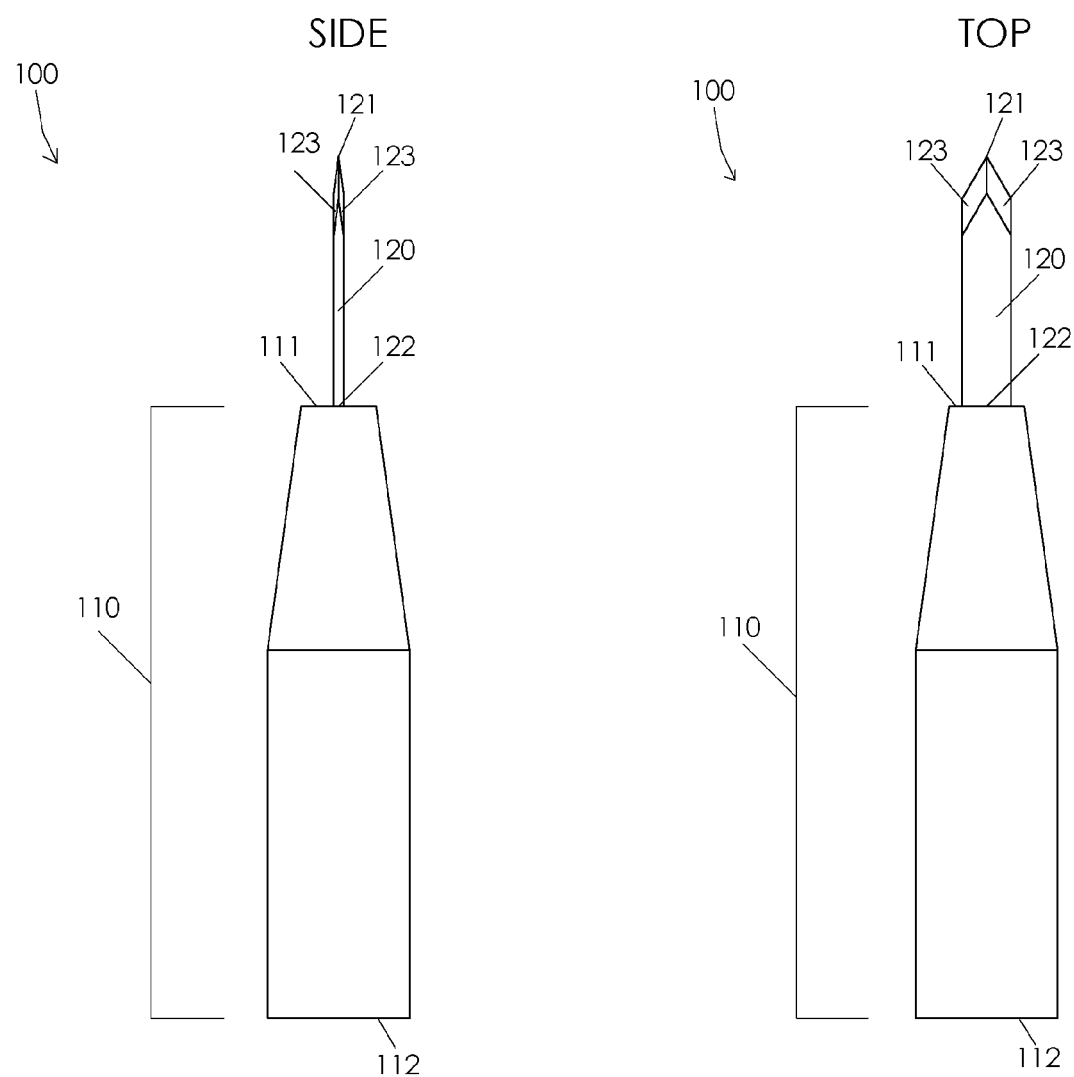

FIGS. 1A and 1B are schematic diagrams illustrating a surgical blade 100. FIG. 1A illustrates a top view, a side view, and a bottom view of surgical blade 100. FIG. 1B illustrates a side view and a top view of surgical blade 100. In one or more embodiments, surgical blade 100 may comprise a blade mount 110 and a blade 120. Illustratively, blade mount 110 is configured to support blade 120. Blade mount 110 comprises a blade mount distal end 111 and a blade mount proximal end 112. In one or more embodiments, blade mount 110 may be configured to orient blade 120 at an angle 130, e.g., for making surgical incisions. Blade mount 110 may be manufactured from any suitable material, e.g., polymers, metals, metal alloys, etc., or from any combination of suitable materials.

Illustratively, blade 120 may be configured to make surgical incisions. Blade 120 comprises a blade distal end 121, a blade proximal end 122, and at least one blade edge 123. In one or more embodiments, blade proximal end 122 interfaces with blade mount distal end 111. Blade 120 may be manufactured from any suitable material, e.g., sapphire, diamond, silicon, polymers, metals, metal alloys, etc., or from any combination of suitable materials.

Figure 2B:
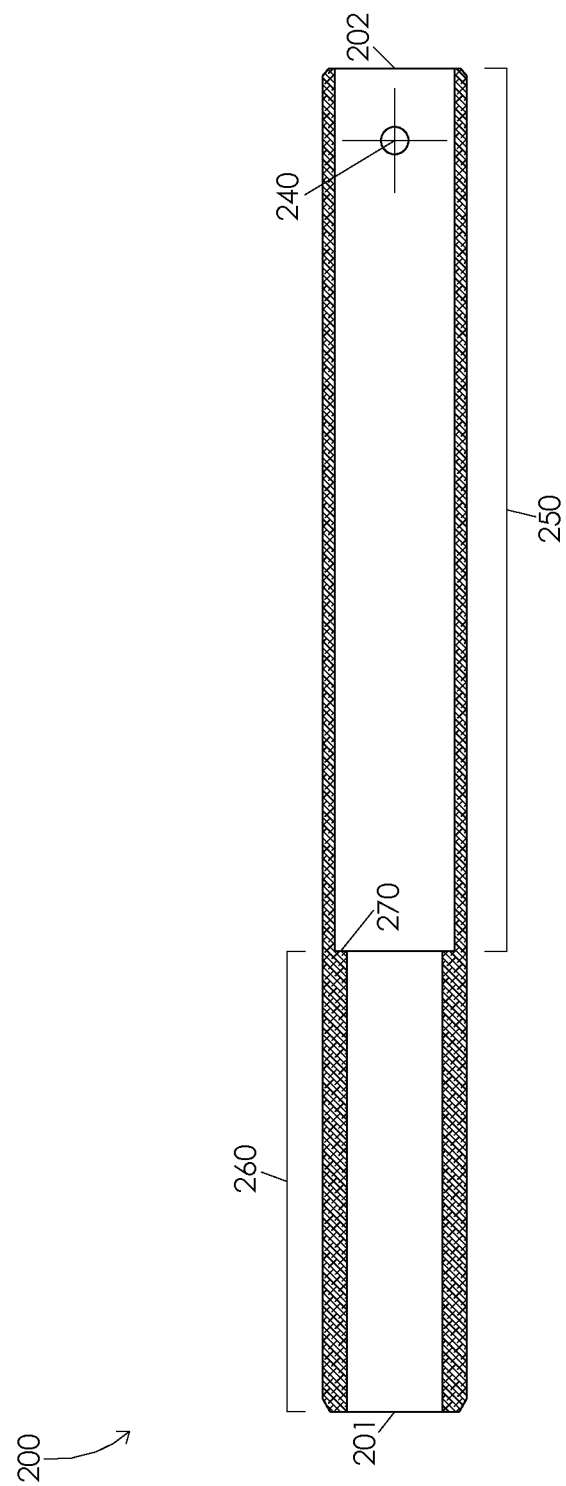
Figure 2C:
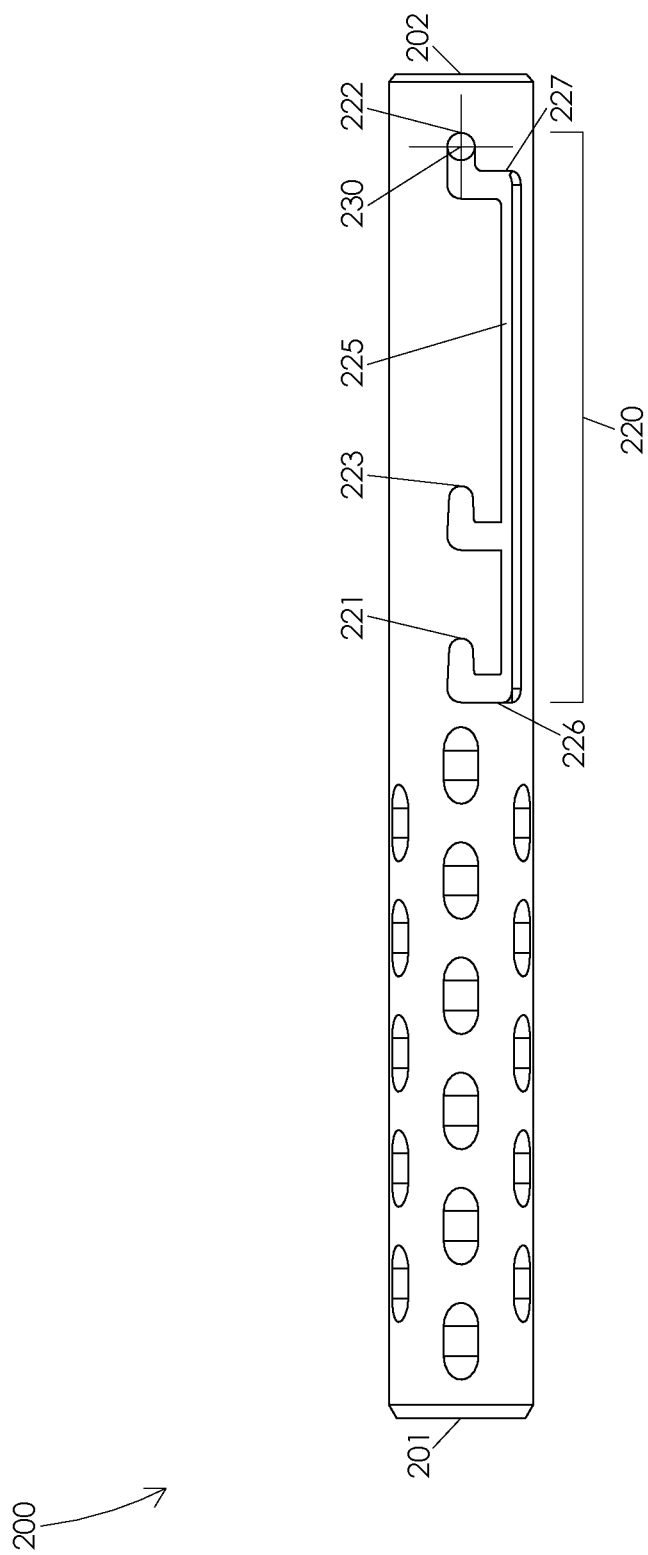

FIGS. 2A, 2B, and 2C are schematic diagrams of an outer sleeve 200. FIG. 2A illustrates a top view, a side view, and a bottom view of outer sleeve 200. In one or more embodiments, outer sleeve 200 may comprise an outer sleeve distal end 201, an outer sleeve proximal end 202, an ergonomic surgical safety grip 210, and an actuation guide 220. Illustratively, ergonomic surgical safety grip 210 may be configured to prevent undesirable movements of surgical blade 100 during a surgical procedure. For example, ergonomic surgical safety grip 210 may be configured to prevent unintentional movements of surgical blade 100 before a surgical procedure, during a surgical procedure, and after a surgical procedure.

In one or more embodiments, ergonomic surgical safety grip 210 may comprise one or more grip points 211. Illustratively, grip points 211 may be configured to conform to a surgeon's finger tips. In one or more embodiments, grip points 211 may be configured to increase a total contact area between a surgeon's finger tips and ergonomic surgical safety grip 210. Illustratively, grip points 211 may be manufactured as one or more indents in outer sleeve 200, e.g., to increase a total contact area between a surgeon's finger tips and ergonomic surgical safety grip 210. In one or more embodiments, grip points 211 may be manufactured as one or more apertures in outer sleeve 200. Illustratively, ergonomic surgical safety grip 210 may comprise a sleeve configured to fit over outer sleeve 200. Ergonomic surgical safety grip 210 may be manufactured from any suitable material, e.g., polymers, metals, metal alloys, etc., or from any combination of suitable materials.

Illustratively, actuation guide 220 may be configured to guide an actuation of surgical blade 100. In one or more embodiments, actuation guide 220 may comprise a distal detent 221, a proximal detent 222, and an actuation channel 225. Actuation channel 225 may comprise an actuation channel distal end 226 and an actuation channel proximal end 227. Illustratively, an actuation pin 230 may be configured to actuate in conjunction with surgical blade 100. In one or more embodiments, distal detent 221 may be configured to temporarily fix actuation pin 230 in a distal position in actuation guide 220, and proximal detent 222 may be configured to temporarily fix actuation pin 230 in a proximal position in actuation guide 220. Illustratively, actuation channel 225 may be configured to allow actuation pin 230 to actuate between a distal position and a proximal position in actuation guide 220. For example, actuation channel 225 may be configured to allow actuation pin 230 to actuate between actuation channel proximal end 227 and actuation channel distal end 226. In one or more embodiments, actuation pin 230 may be accessed, e.g., for replacement, repair, etc., via an actuation pin access port 240.

FIG. 2B illustrates a view of a cross-section of outer sleeve 200. In one or more embodiments, an interior of outer sleeve 200 may comprise an outer sleeve proximal core 250, outer sleeve distal core 260, and a pressure mechanism distal interface 270. Illustratively, outer sleeve distal core 260 may be configured to conform to blade mount 110.

FIG. 2C illustrates a top view of outer sleeve 200. In one or more embodiments, actuation guide 220 may comprise a distal detent 221, a proximal detent 222, and an intermediate detent 223. Illustratively, proximal detent 222 may be configured to fix actuation pin 230 in an intermediate position in actuation guide 220.

Figure 3:
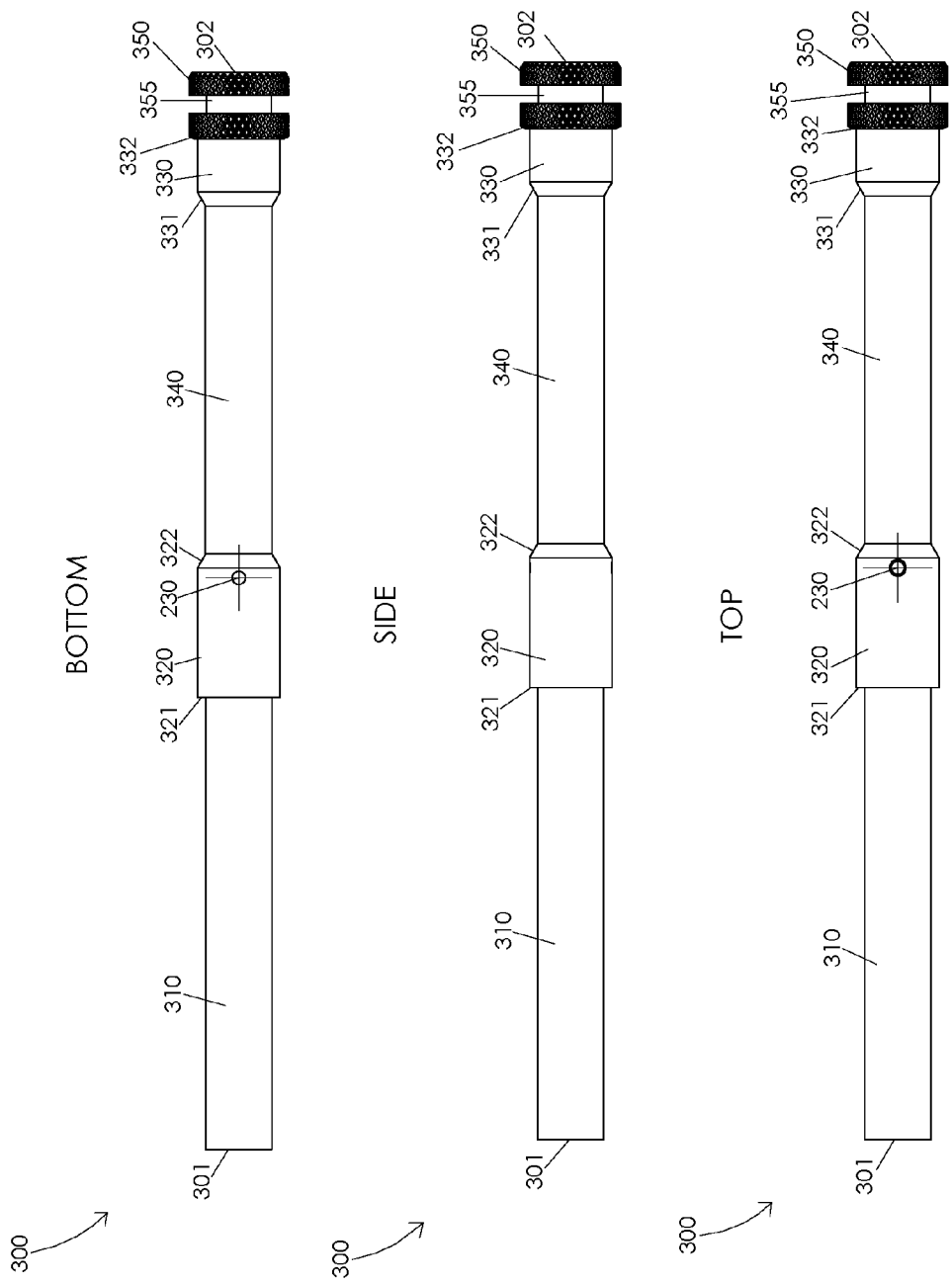
FIG. 3 is a schematic diagram of an inner handle.

FIG. 3 is a schematic diagram of an inner handle 300. FIG. 3 illustrates a top view, a side view, and a bottom view of inner handle 300. Inner handle 300 comprises an inner handle distal end 301 and an inner handle proximal end 302. Illustratively, inner handle 300 may be configured to actuate relative to outer sleeve 200. In one or more embodiments, inner handle 300 may comprise a pressure mechanism foundation 310, a distal outer sleeve interface 320, a proximal outer sleeve interface 330, an inner handle base 340, and an actuation control apparatus 350. Illustratively, distal outer sleeve interface 320 and proximal outer sleeve interface 330 may be configured to conform to the dimensions of outer sleeve proximal core 250.

In one or more embodiments, distal outer sleeve interface 320 may be configured to contain actuation pin 230. Illustratively, distal outer sleeve interface 320 may comprise a pressure mechanism proximal interface 321 and a distal actuation guide 322. In one or more embodiments, distal actuation guide 322 may be configured to minimize a friction force during an actuation of inner handle 300. Illustratively, proximal outer sleeve interface 330 may comprise a proximal actuation guide 331 and an actuation control apparatus interface 332. In one or more embodiments, proximal actuation guide 331 may be configured to minimize a friction force during an actuation of inner handle 300.

In one or more embodiments, actuation control apparatus 350 may be configured to initiate an actuation of surgical blade 100. Illustratively, actuation control apparatus 350 may be configured to manipulate an actuation of surgical blade 100. For example, actuation control apparatus 350 may be configured to control a lateral actuation of surgical blade 100 relative to outer sleeve 200. In one or more embodiments, actuation control apparatus 350 may be configured to control a rotational actuation of surgical blade 100 relative to outer sleeve 200. Illustratively, actuation control apparatus 350 may comprise a diamond or knurl grip pattern configured to improve a surgeon's or an assistant's ability to grasp actuation control apparatus 350. Actuation control apparatus 350 may be manufactured from any suitable material, e.g., polymers, metals, metal alloys, etc., or from any combination of suitable materials.

In one or more embodiments, actuation control apparatus 350 may comprise a blade indication signal 355. Illustratively, blade indication signal 355 may be a visual signal, e.g., a color, configured to indicate one or more properties of surgical blade 100. In one or more embodiments, blade indication signal 355 may comprise a solid or multicolored mark configured to indicate one or more properties of blade 120. For example, a particular color or color combination displayed by blade indication signal 355 may indicate a particular property of blade 120, e.g., a length of blade 120, a width of blade 120, a surgical geometry of blade 120, a composition material of blade 120, etc. Illustratively, blade indication signal 355 may be configured to display specific colors wherein the colors yellow, beige, black, blue, red, brown, green, and grey may indicate blade 120 dimension lengths of 1.0 mm, 1.8 mm, 2.2 mm, 2.4 mm, 2.65 mm, 2.8 mm, 3.0 mm, and 3.2 mm, respectively.

Figure 4:
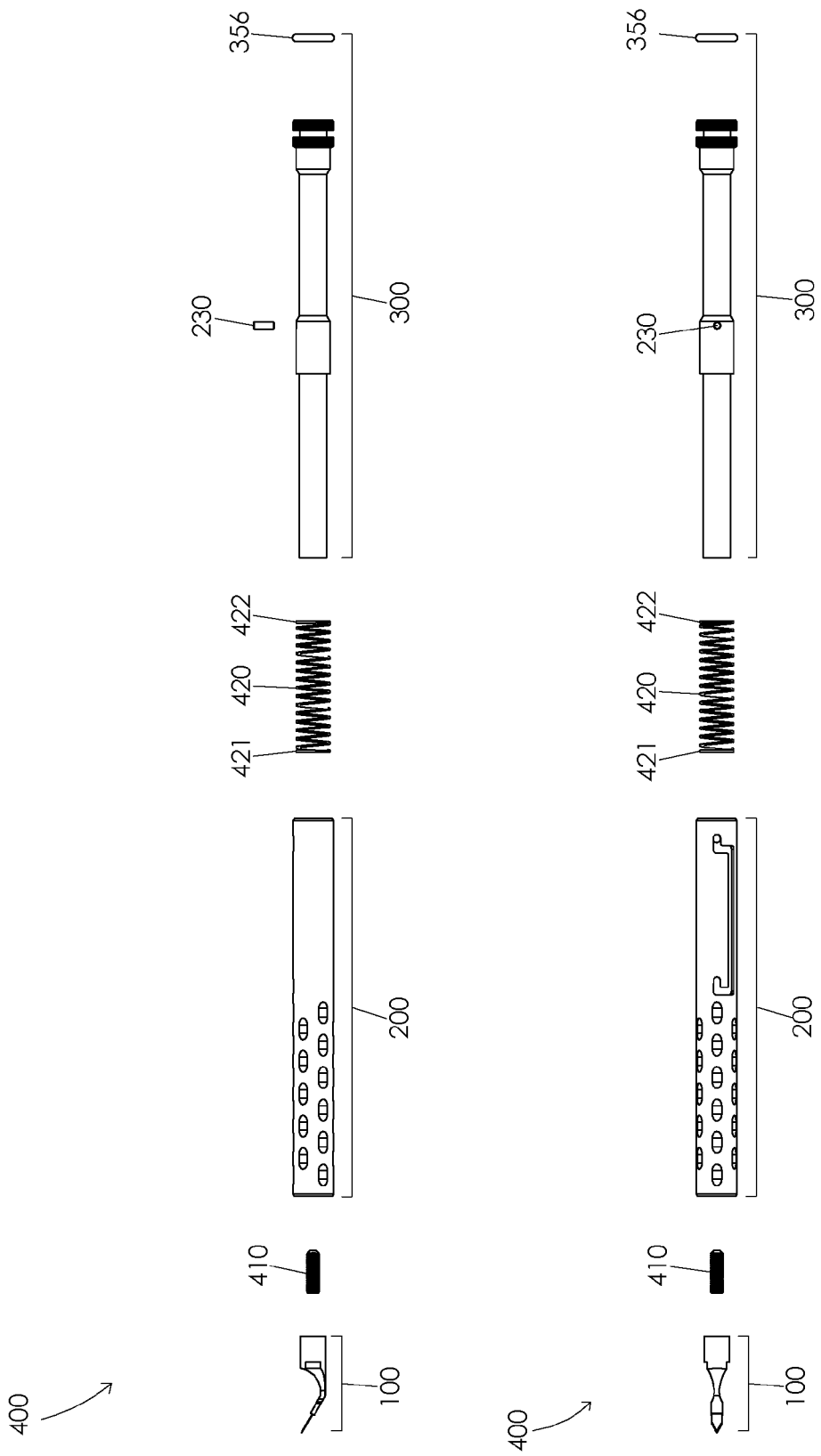
FIG. 4 is a schematic diagram of an exploded view of a surgical instrument handle.

FIG. 4 is a schematic diagram of an exploded view of a surgical instrument handle 400. FIG. 4 illustrates an exploded top view and an exploded side view of surgical instrument handle 400. In one or more embodiments, surgical instrument handle 400 may comprise a surgical blade 100, an outer sleeve 200, an actuation pin 230, an inner handle 300, a fixation mechanism 410, and a pressure mechanism 420. Illustratively, fixation mechanism 410 is configured to attach blade mount proximal end 112 and inner handle distal end 301. In one or more embodiments, fixation mechanism 410 may comprise a set screw configured to firmly attach blade mount proximal end 112 to inner handle distal end 301. In one or more embodiments, fixation mechanism 410 may comprise an adhesive material configured to attach blade mount proximal end 112 to inner handle distal end 301, or fixation mechanism 410 may comprise one or more magnets configured to attach blade mount proximal end 112 to inner handle distal end 301.

Illustratively, pressure mechanism 420 may comprise a pressure mechanism distal end 421 and a pressure mechanism proximal end 422. In one or more embodiments, surgical instrument handle 400 may be assembled by fitting pressure mechanism 420 on pressure mechanism foundation 310 by, e.g., guiding pressure mechanism proximal end 422 over inner handle distal end 301 until pressure mechanism proximal end 422 abuts pressure mechanism proximal interface 321. Illustratively, pressure mechanism 420 may be disposed between pressure mechanism distal interface 270 and pressure mechanism proximal interface 321. For example, pressure mechanism distal end 421 may abut pressure mechanism distal interface 270 and pressure mechanism proximal end 422 may abut pressure mechanism proximal interface 321. In one or more embodiments, pressure mechanism 420 may be coupled to pressure mechanism foundation 310. For example, pressure mechanism 420 and pressure mechanism foundation 310 may be manufactured from a single suitable material or a combination of suitable materials.

Illustratively, pressure mechanism 420 may be configured to provide a force. In one or more embodiments, pressure mechanism 420 may be configured to provide a constant or uniform force. In one or more other embodiments, pressure mechanism 420 may be configured to provide a variable force. For example, pressure mechanism 420 may comprise a spring or a coil. In one or more embodiments, pressure mechanism 420 may comprise a spring with a spring constant in a range of 0.01 N/mm to 5.0 N/mm. In one or more other embodiments, pressure mechanism 420 may comprise a spring with a spring constant less than 0.01 N/mm or greater than 5.0 N/mm. Illustratively, pressure mechanism 420 may comprise a pneumatic system. In one or more embodiments, pressure mechanism 420 may be configured to provide a resistive force to resist an actuation. For example, pressure mechanism 420 may be configured to provide a resistive force to resist an actuation of surgical blade 100 from an enclosed position wherein surgical blade 100 is contained within outer sleeve 200 to an extended position wherein surgical blade 100 is at least partially extended from outer sleeve distal end 201. Illustratively, pressure mechanism 420 may be configured to provide a resistive force that resists actuation pin 230 from an egression out of distal detent 221 or proximal detent 222. In one or more embodiments, pressure mechanism 420 may be configured to provide a facilitating force to facilitate an actuation. For example, pressure mechanism 420 may be configured to provide a facilitating force to facilitate an actuation of surgical blade 100 from an extended position wherein surgical blade 100 is at least partially extended from outer sleeve distal end 201 to an enclosed position wherein surgical blade 100 is contained within outer sleeve 200.

In one or more embodiments, blade indication signal 355 may comprise a blade indication band 356. Illustratively, blade indication band 356 may be configured to fit over a portion of actuation control apparatus 350. For example, blade indication band 356 may be a single color or a combination of single colors configured to indicate one or more properties of surgical blade 100. Illustratively, a blade indication band 356 of a particular color or color combination may indicate a particular property of blade 120, e.g., a length of blade 120, a width of blade 120, a surgical geometry of blade 120, a composition material of blade 120, etc.

Figure 5:
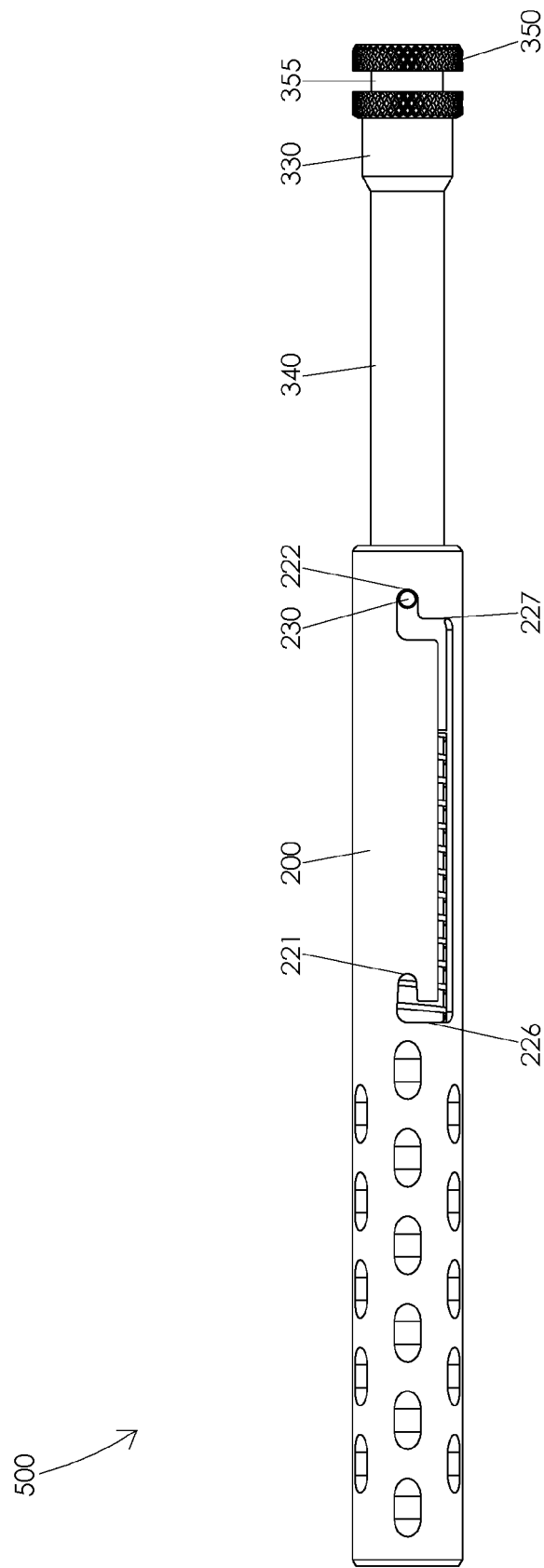
FIG. 5 is a schematic diagram illustrating a surgical blade in a safe position.

FIG. 5 is a schematic diagram illustrating a surgical blade 100 in a safe position 500. In one or more embodiments, surgical blade 100 may be in safe position 500 when actuation pin 230 is temporarily fixed in proximal detent 222. Illustratively, surgical blade 100 may be contained in outer sleeve 200 when actuation pin 230 is temporarily fixed in proximal detent 222. In one or more embodiments, pressure mechanism 420 may be configured to provide a resistive force that resists actuation pin 230 from an egression out of proximal detent 222.

Figure 6:
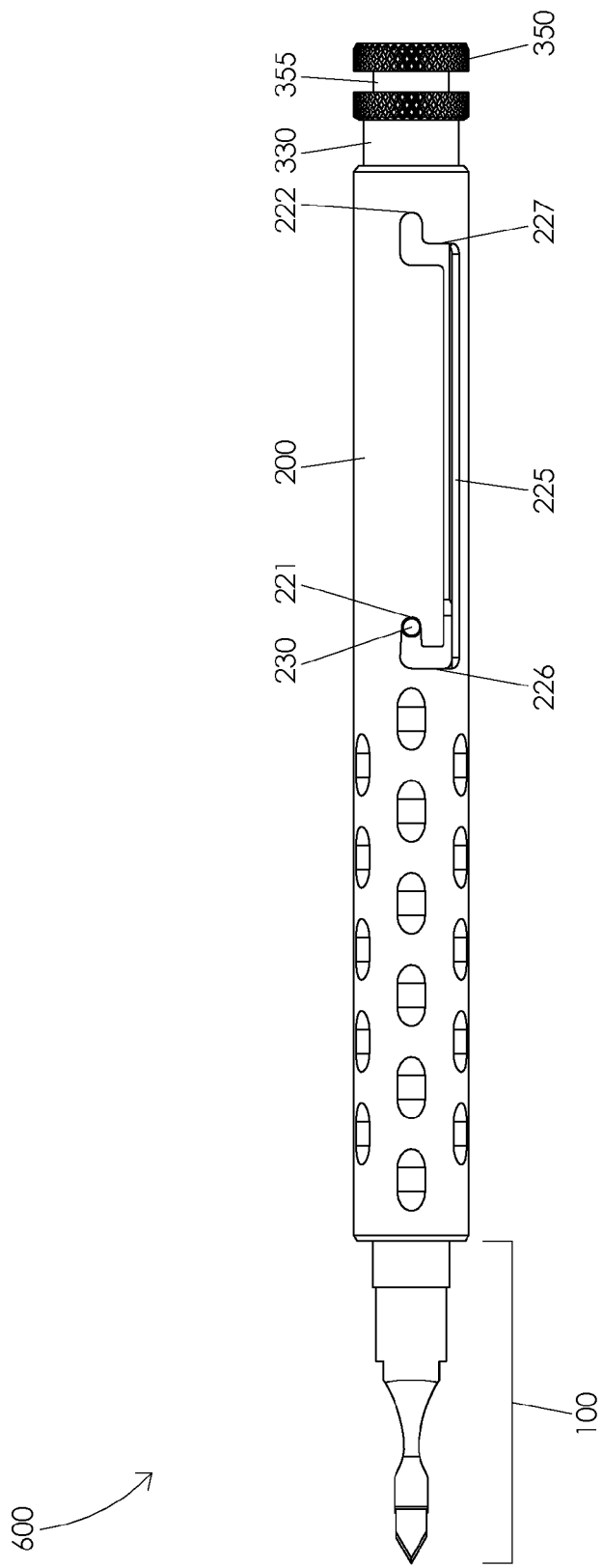
FIG. 6 is a schematic diagram illustrating a surgical blade in a surgical position.

FIG. 6 is a schematic diagram illustrating a surgical blade 100 in a surgical position 600. In one or more embodiments, surgical blade 100 may be in surgical position 600 when actuation pin 230 is temporarily fixed in distal detent 221. Illustratively, surgical blade 100 may extend from outer sleeve distal end 201 when actuation pin 230 is temporarily fixed in distal detent 221. In one or more embodiments, pressure mechanism 420 may be configured to provide a resistive force that resists actuation pin 230 from an egression out of distal detent 221.

Figure 7A:
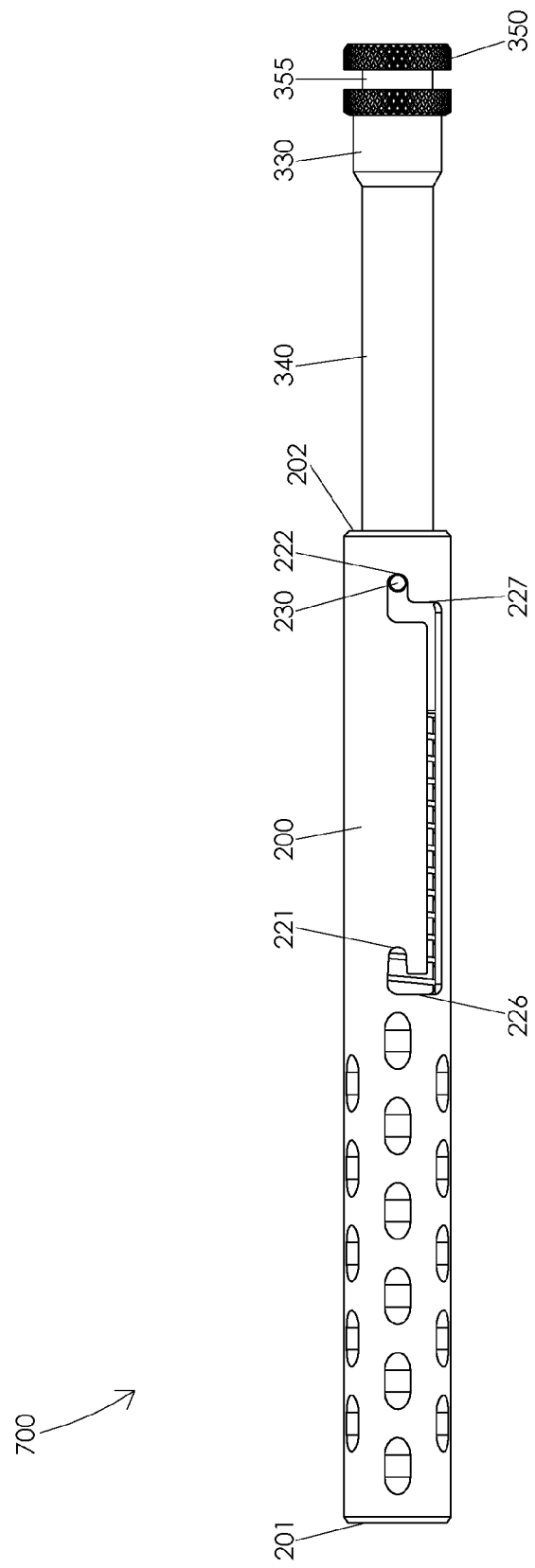
FIGS. 7A, 7B, 7C, 7D, 7E, 7F, and 7G are schematic diagrams illustrating an actuation of a surgical blade from a first fixed position to a second fixed position.

FIGS. 7A, 7B, 7C, 7D, 7E, 7F, and 7G are schematic diagrams illustrating an actuation of a surgical blade 100 from a first fixed position 700 to a second fixed position 760. FIG. 7A illustrates a surgical blade 100 in a first fixed position 700. Illustratively, first fixed position 700 may comprise a safe position 500 wherein surgical blade 100 may be contained within outer sleeve 200. For example, in first fixed position 700, actuation pin 230 may be temporarily fixed in proximal detent 222.

Figure 7B:
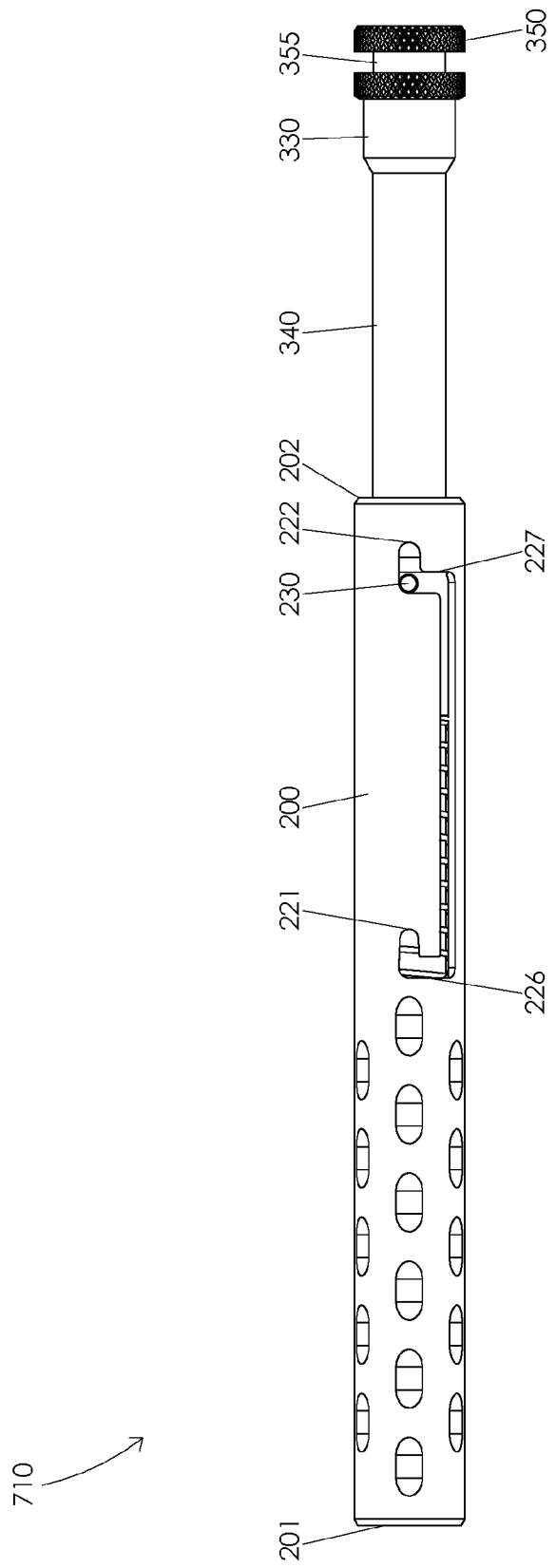

FIG. 7B illustrates an egress 710 of actuation pin 230 from proximal detent 222. Illustratively, egress 710 of actuation pin 230 from proximal detent 222 may be accomplished by an application of a force vector, e.g., applied to actuation control apparatus 350, with a direction oriented toward outer sleeve distal end 201. For example, a surgeon or a surgeon's assistant may cause an egress 710 of actuation pin 230 from proximal detent 222 by, e.g., grasping actuation control apparatus 350 and pushing inner handle 300 into outer sleeve 200. In one or more embodiments, pressure mechanism 420 may be configured to provide a resistive force that resists an egress 710 of actuation pin 230 out of proximal detent 222.

Figure 7C:
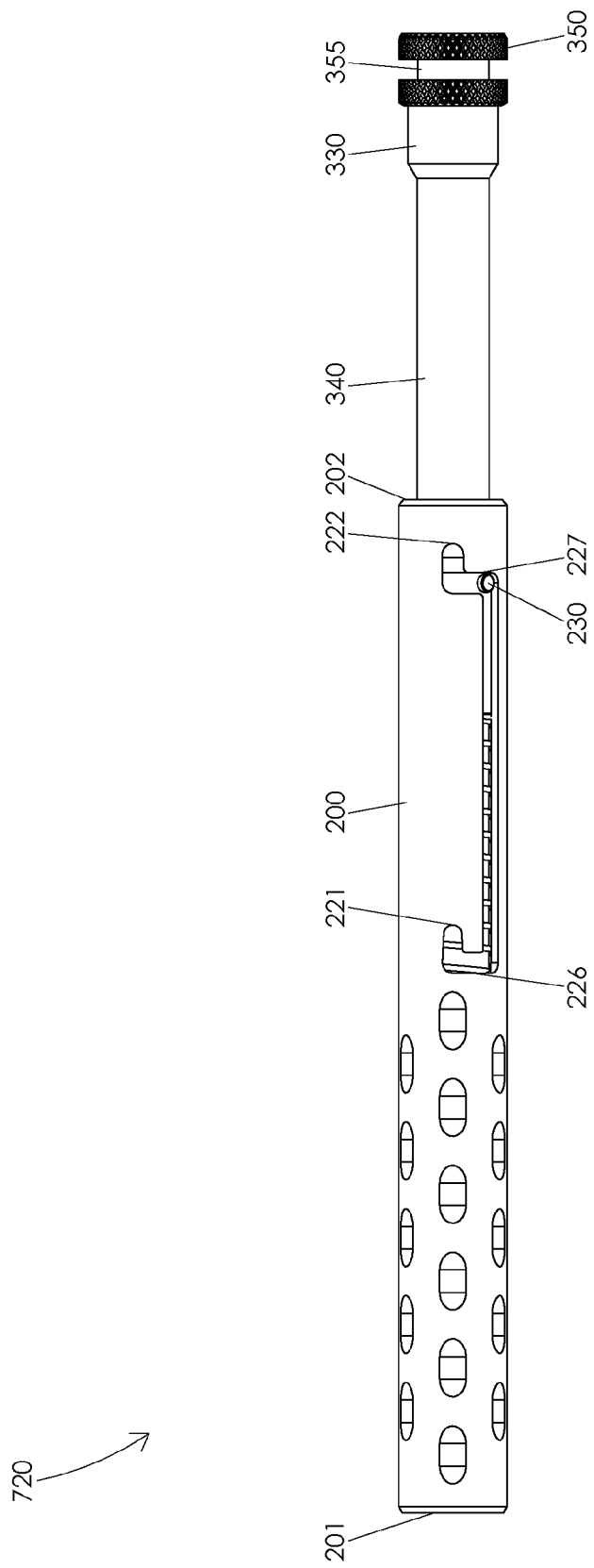

FIG. 7C illustrates an ingress 720 of actuation pin 230 into actuation channel 225. Illustratively, ingress 720 of actuation pin 230 into actuation channel 225 may be accomplished by a rotation of actuation control apparatus 350 after an egress 710 of actuation pin 230 from proximal detent 222. For example, after causing an egress 710 of actuation pin 230 from proximal detent 222, a surgeon or a surgeon's assistant may cause an ingress 720 of actuation pin 230 into actuation channel 225 by, e.g., grasping actuation control apparatus 350 and rotating inner handle 300 relative to outer sleeve 200.

Figure 7D:
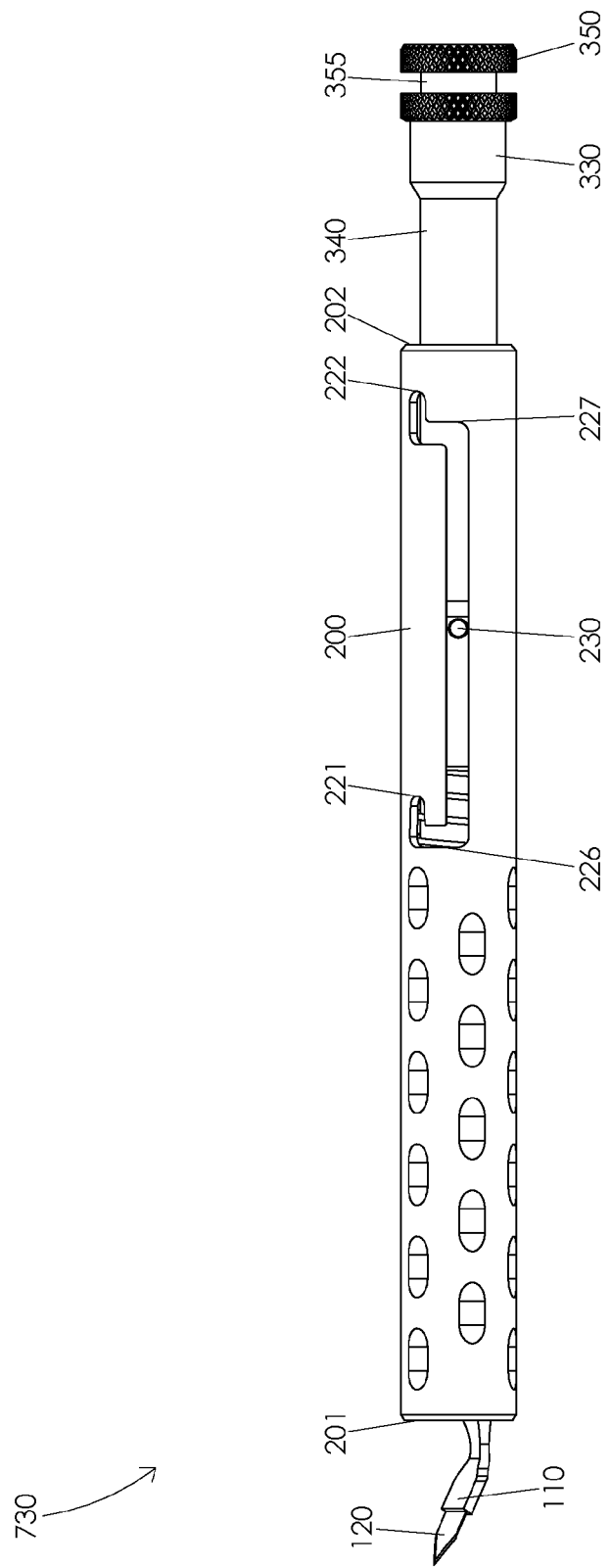

FIG. 7D illustrates an actuation 730 of actuation pin 230 along actuation channel 225, e.g., away from actuation channel proximal end 227 and toward actuation channel distal end 226. Illustratively, an actuation 730 of actuation pin 230 along actuation channel 225 may be accomplished by an application of a force vector, e.g., applied to actuation control apparatus 350, with a direction oriented toward outer sleeve distal end 201 after an ingress 720 of actuation pin 230 into actuation channel 225. For example, after causing an ingress 720 of actuation pin 230 into actuation channel 225, a surgeon or a surgeon's assistant may cause an actuation 730 of actuation pin 230 along actuation channel 225 by, e.g., grasping actuation control apparatus 350 and pushing inner handle 300 into outer sleeve 200. In one or more embodiments, pressure mechanism 420 may be configured to provide a resistive force that resists an actuation 730 of actuation pin 230 along actuation channel 225.

Figure 7E:
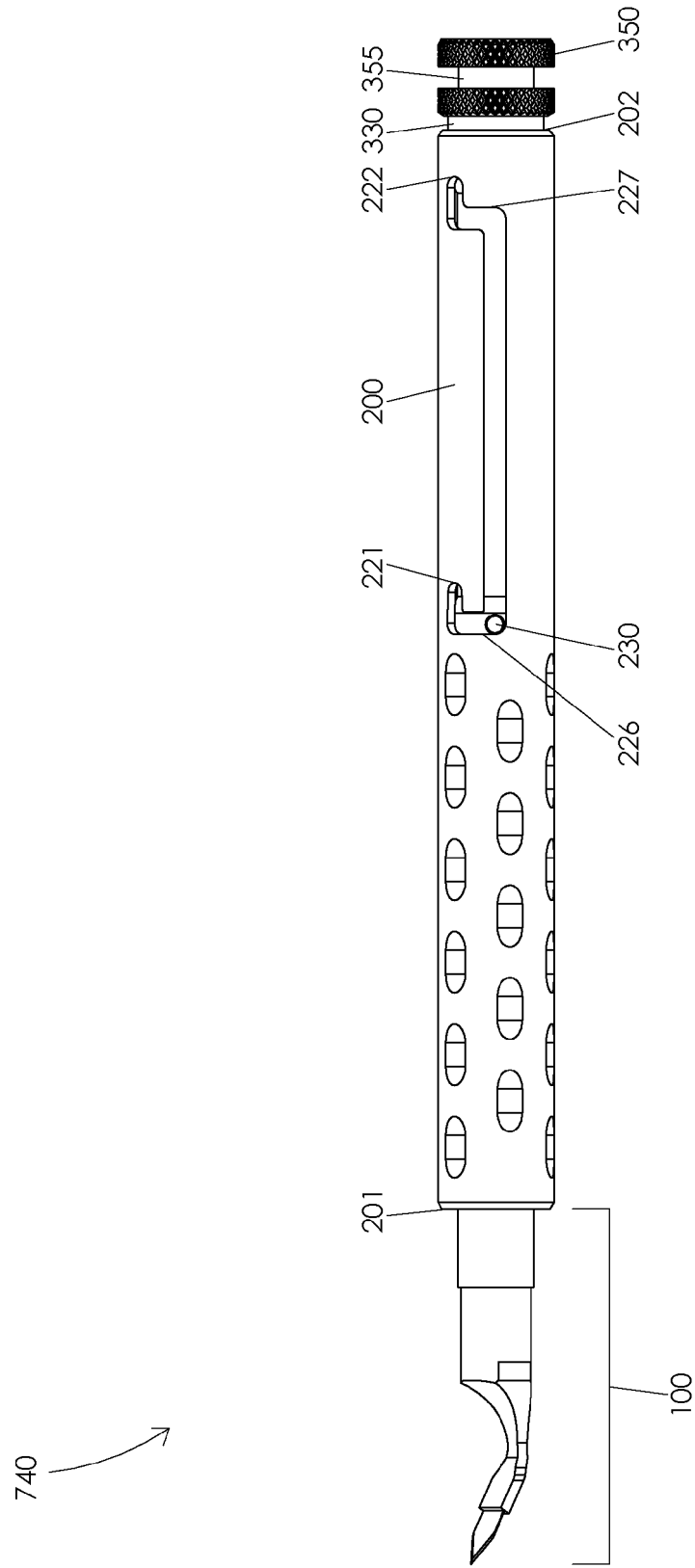

FIG. 7E illustrates an ingress alignment 740 of actuation pin 230 with distal detent 221. Illustratively, ingress alignment 740 of actuation pin 230 with distal detent 221 may be accomplished by guiding an actuation 730 of actuation pin 230 to actuation channel distal end 226.

Figure 7F:
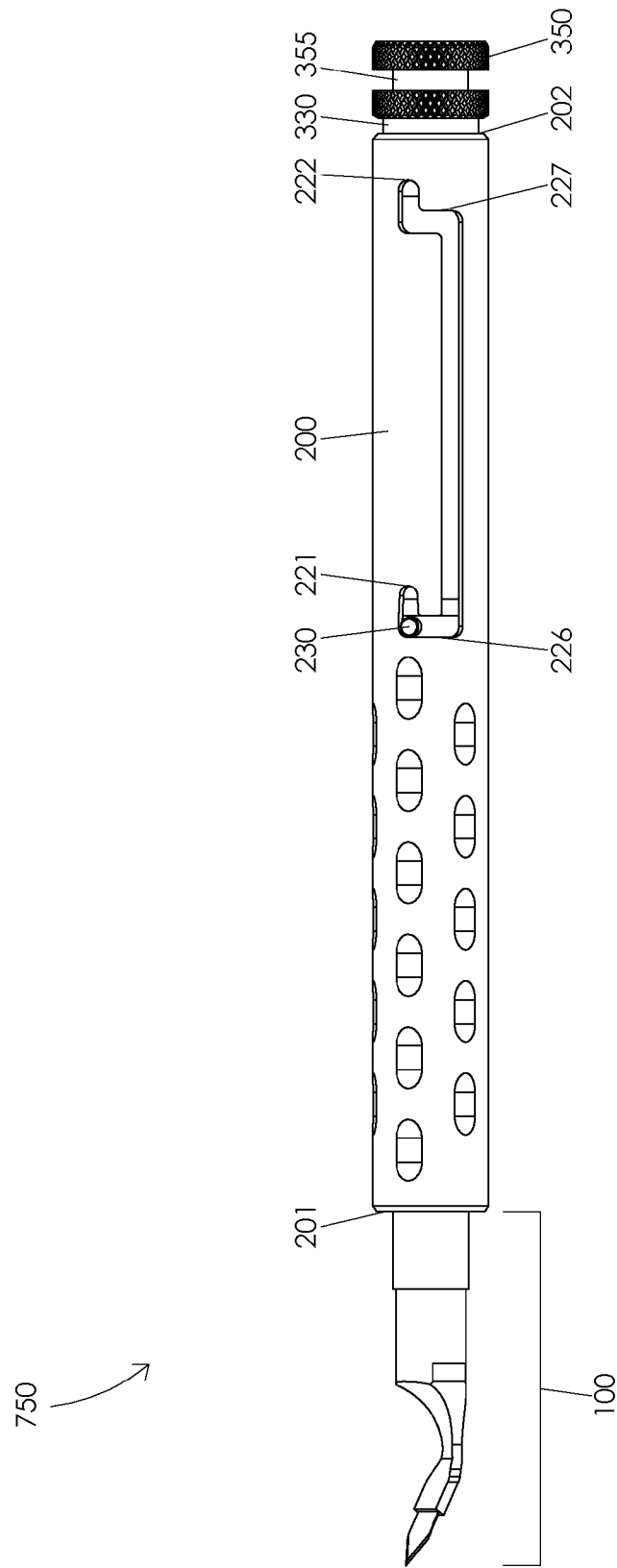

FIG. 7F illustrates actuation pin 230 in a position for ingress 750 into distal detent 221. Illustratively, actuation pin 230 may be guided to position for ingress 750 into distal detent 221 by a rotation of actuation control apparatus 350 after an ingress alignment 740 of actuation pin 230 with distal detent 221. For example, after causing an ingress alignment 740 of actuation pin 230 with distal detent 221, a surgeon or a surgeon's assistant may guide actuation pin 230 to position for ingress 750 into distal detent 221 by, e.g., grasping actuation control apparatus 350 and rotating inner handle 300 relative to outer sleeve 200.

Figure 7G:
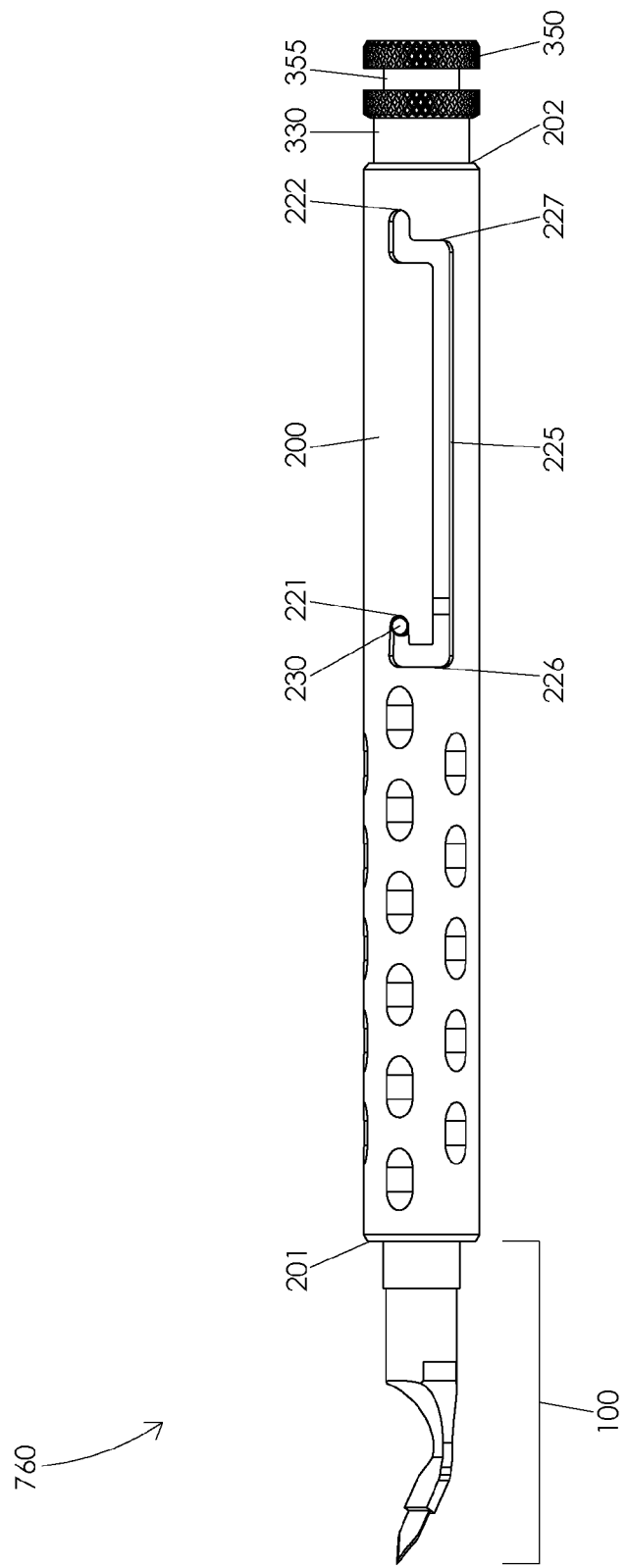

FIG. 7G illustrates a surgical blade 100 in a second fixed position 760. Illustratively, surgical blade 100 may be temporarily fixed in a second fixed position 760 by an application of a force vector, e.g., applied to actuation control apparatus 350, with a direction oriented toward outer sleeve proximal end 202 after actuation pin 230 is in position for ingress 750 into distal detent 221. For example, after guiding actuation pin 230 to position for ingress 750 into distal detent 221, a surgeon or a surgeon's assistant may temporarily fix surgical blade 100 in a second fixed position 760 by, e.g., grasping actuation control apparatus 350 and pulling inner handle 300 out of outer sleeve 200. In one or more embodiments, pressure mechanism 420 may be configured to provide a facilitating force that facilitates an actuation of actuation pin 230 from position for ingress 750 to a second fixed position 760.

Figure 8A:
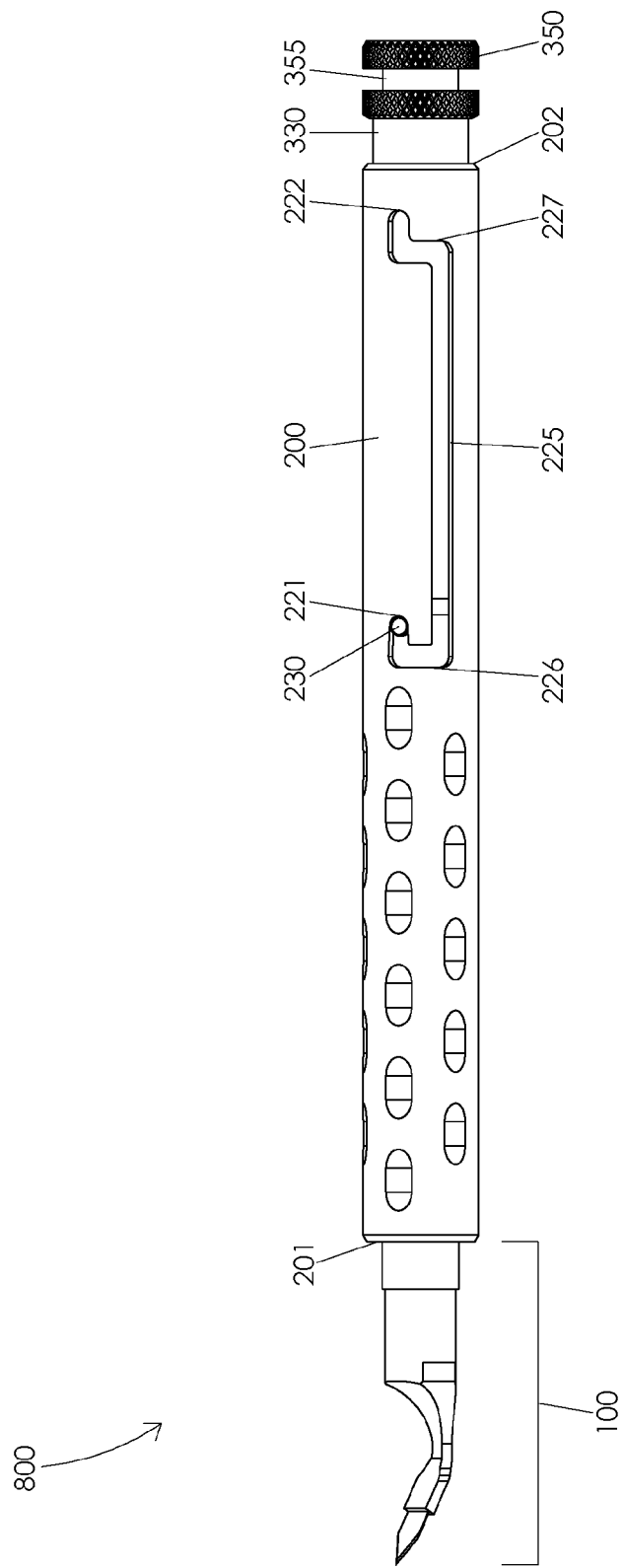
FIGS. 8A, 8B, 8C, 8D, 8E, 8F, and 8G are schematic diagrams illustrating an actuation of a surgical blade from a second fixed position to a first fixed position.

FIGS. 8A, 8B, 8C, 8D, 8E, 8F, and 8G are schematic diagrams illustrating an actuation of a surgical blade from a second fixed position 760 to a first fixed position 700. FIG. 8A illustrates a surgical blade 100 in a second fixed position 760. Illustratively, second fixed position 760 may comprise a surgical position 600 wherein surgical blade 100 may be at least partially extended from outer sleeve 200. For example, surgical blade 100 may be in second fixed position 760 when actuation pin 230 is temporarily fixed in distal detent 221.

Figure 8B:
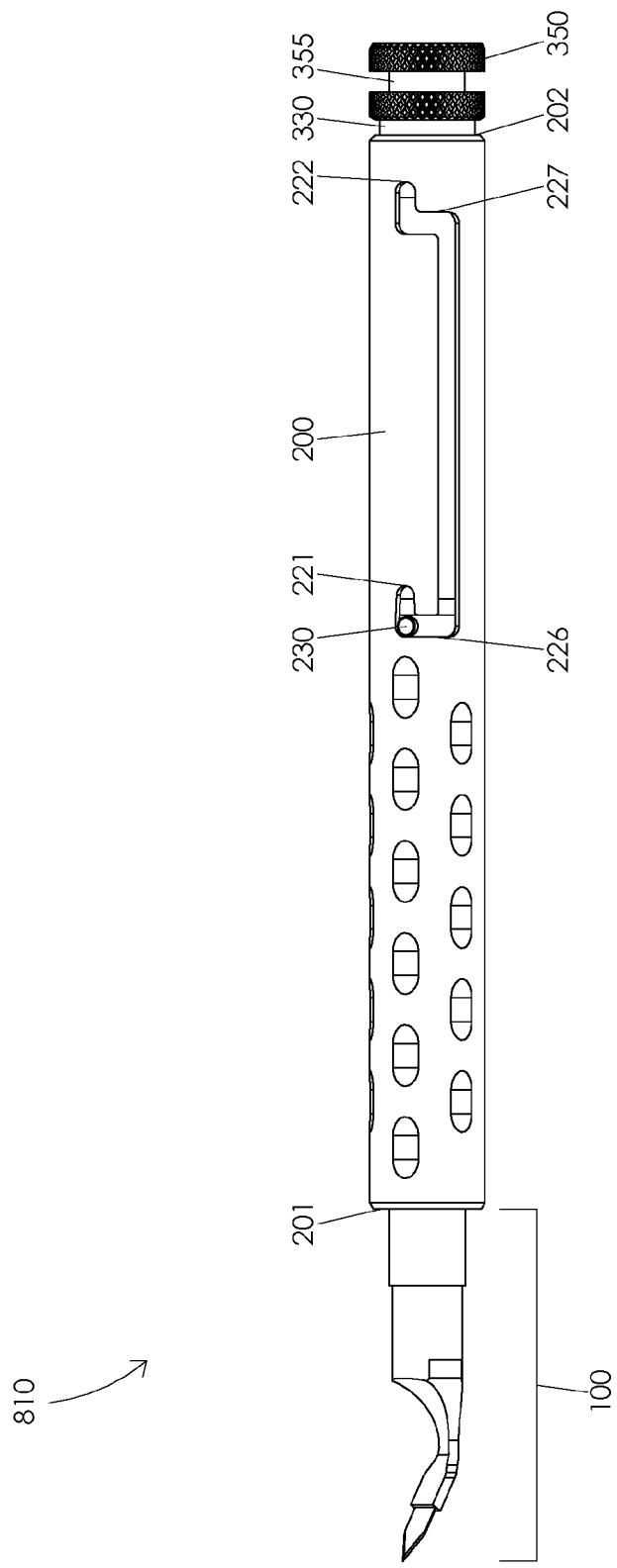

FIG. 8B illustrates an egress 810 of actuation pin 230 from distal detent 221. Illustratively, egress 810 of actuation pin 230 from distal detent 221 may be accomplished by an application of a force vector, e.g., applied to actuation control apparatus 350, with a direction oriented toward outer sleeve distal end 201. For example, a surgeon or a surgeon's assistant may cause an egress 810 of actuation pin 230 from distal detent 222 by, e.g., grasping actuation control apparatus 350 and pushing inner handle 300 into outer sleeve 200. In one or more embodiments, pressure mechanism 420 may be configured to provide a resistive force that resists an egress 810 of actuation pin 230 out of distal detent 221.

Figure 8C:
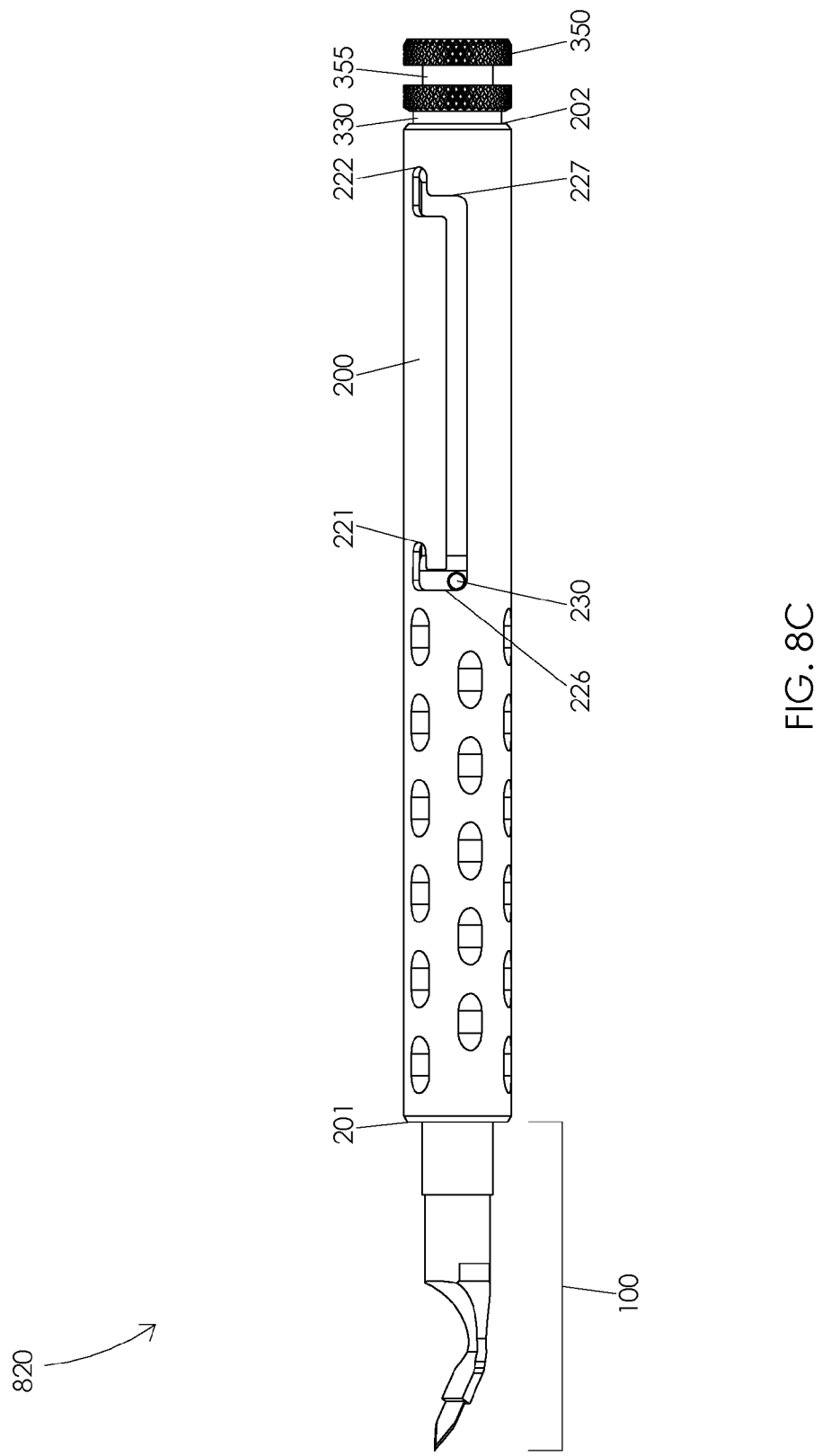

FIG. 8C illustrates an ingress 820 of actuation pin 230 into actuation channel 225. Illustratively, ingress 820 of actuation pin 230 into actuation channel 225 may be accomplished by a rotation of actuation control apparatus 350 after an egress 810 of actuation pin 230 from distal detent 221. For example, after causing an egress 810 of actuation pin 230 from distal detent 221, a surgeon or a surgeon's assistant may cause an ingress 820 of actuation pin 230 into actuation channel 225 by, e.g., grasping actuation control apparatus 350 and rotating inner handle 300 relative to outer sleeve 200.

Figure 8D:
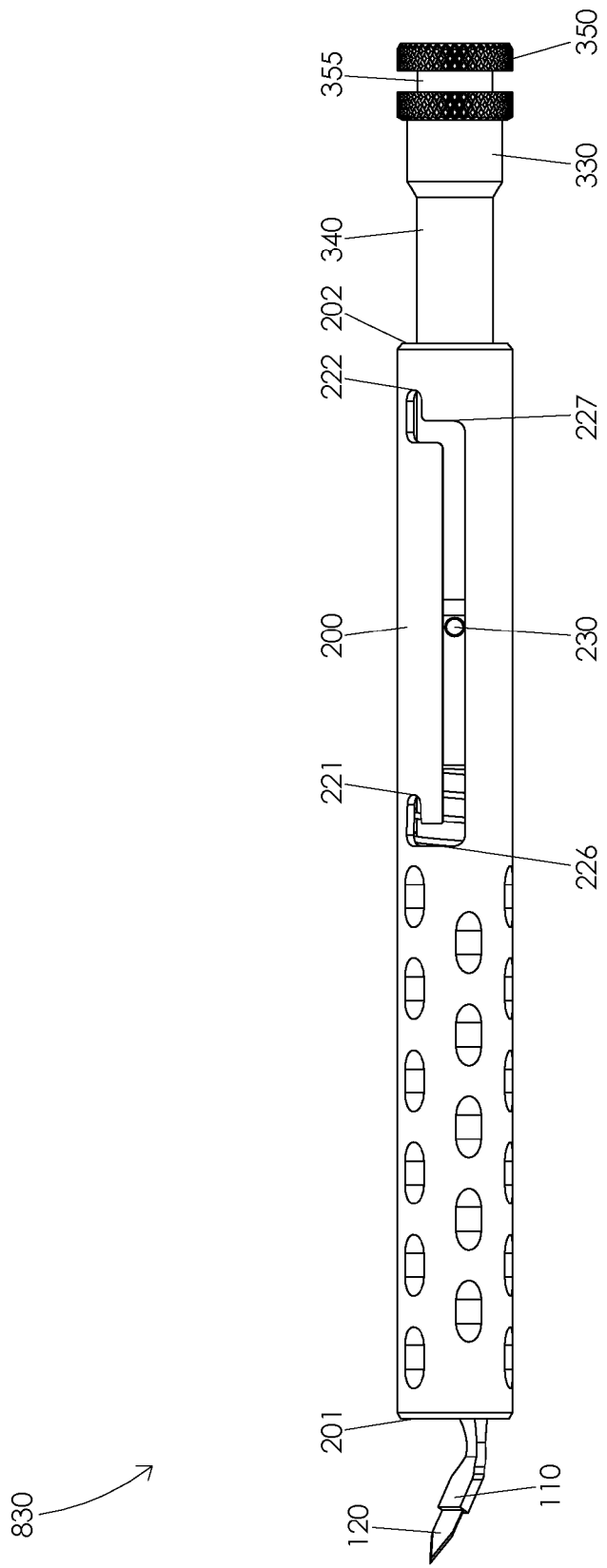

FIG. 8D illustrates an actuation 830 of actuation pin 230 along actuation channel 225, e.g., away from actuation channel distal end 226 and toward actuation channel proximal end 227. Illustratively, an actuation 830 of actuation pin 230 along actuation channel 225 may be accomplished by an application of a force vector, e.g., applied to actuation control apparatus 350, with a direction oriented toward inner handle proximal end 302 after an ingress 820 of actuation pin 230 into actuation channel 225. For example, after causing an ingress 820 of actuation pin 230 into actuation channel 225, a surgeon or a surgeon's assistant may cause an actuation 830 of actuation pin 230 along actuation channel 225 by, e.g., grasping actuation control apparatus 350 and pulling inner handle 300 out of outer sleeve 200. In one or more embodiments, pressure mechanism 420 may be configured to provide a facilitating force that facilitates an actuation 830 of actuation pin 230 along actuation channel 225.

Figure 8E:
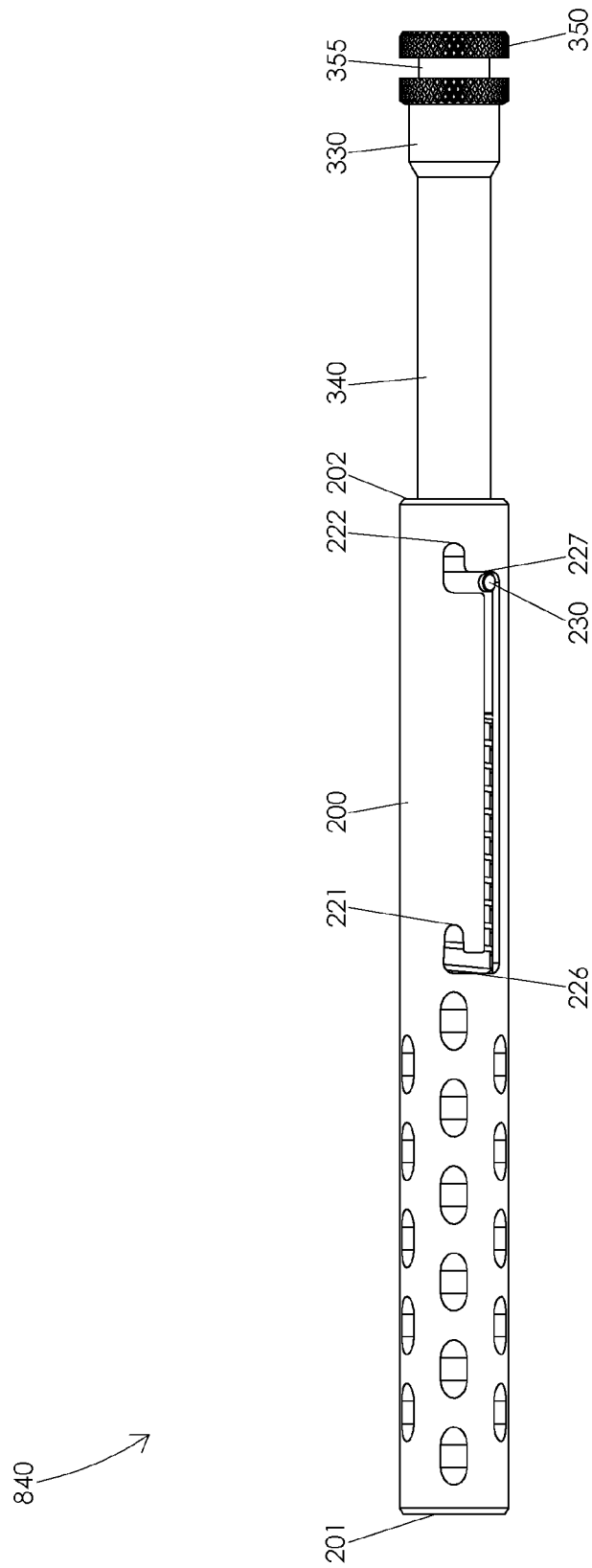

FIG. 8E illustrates an ingress alignment 840 of actuation pin 230 with proximal detent 222. Illustratively, ingress alignment 840 of actuation pin 230 with proximal detent 222 may be accomplished by guiding an actuation 830 of actuation pin 230 to actuation channel proximal end 227.

Figure 8F:
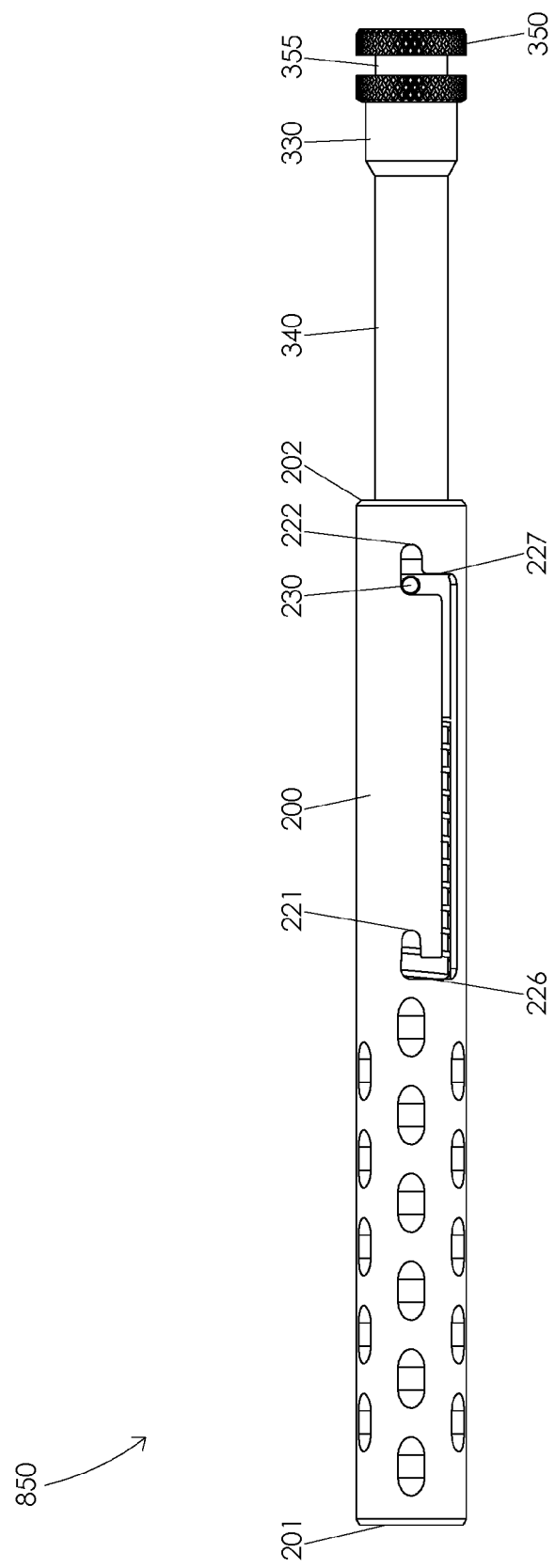

FIG. 8F illustrates actuation pin 230 in a position for ingress 850 into proximal detent 222. Illustratively, actuation pin 230 may be guided to position for ingress 850 into proximal detent 222 by a rotation of actuation control apparatus 350 after an ingress alignment 840 of actuation pin 230 with proximal detent 222. For example, after causing an ingress alignment 840 of actuation pin 230 with proximal detent 222, a surgeon or a surgeon's assistant may guide actuation pin 230 to position for ingress 850 into proximal detent 222 by, e.g., grasping actuation control apparatus 350 and rotating inner handle 300 relative to outer sleeve 200.

Figure 8G:
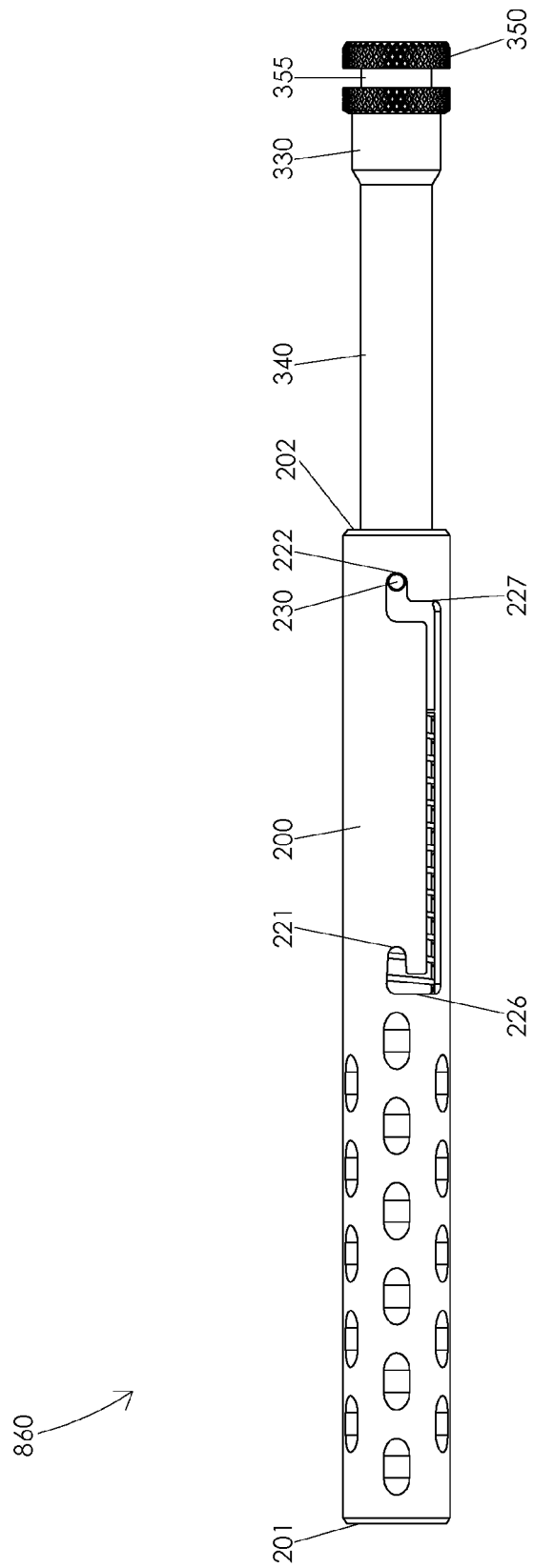

FIG. 8G illustrates a surgical blade 100 in a first fixed position 700. Illustratively, surgical blade 100 may be temporarily fixed in a first fixed position 700 by an application of a force vector, e.g., applied to actuation control apparatus 350, with a direction oriented toward inner handle proximal end 302 after actuation pin 230 is in position for ingress 850 into proximal detent 222. For example, after guiding actuation pin 230 to position for ingress 850 into proximal detent 222, a surgeon or a surgeon's assistant may temporarily fix surgical blade 100 in a first fixed position 700 by, e.g., grasping actuation control apparatus 350 and pulling inner handle 300 out of outer sleeve 200. In one or more embodiments, pressure mechanism 420 may be configured to provide a facilitating force that facilitates an actuation of actuation pin 230 from position for ingress 850 to a first fixed position 700.

In one or more embodiments, actuation guide 220 may comprise a distal detent 221, a proximal detent 222, and an intermediate detent 223. Illustratively, intermediate detent 223 may be configured to temporarily fix surgical blade 100 in a third fixed position relative to outer sleeve 200; distal detent 221 may be configured to temporarily fix surgical blade 100 in a second fixed position 760 relative to outer sleeve 200; and proximal detent 222 may be configured to temporarily fix surgical blade 100 in a first fixed position 700 relative to outer sleeve 200. For example, while temporarily fixed in a third fixed position relative to outer sleeve 200, surgical blade 100 may extend a first distance from outer sleeve distal end 201. Illustratively, while temporarily fixed in a second fixed position 760 relative to outer sleeve 200, surgical blade 100 may extend a second distance from outer sleeve distal end 201, wherein the second distance from outer sleeve distal end 201 may be greater than the first distance from outer sleeve distal end 201.

In one or more embodiments, intermediate detent 223 may be configured to temporarily fix surgical blade 100 in a first position relative to outer sleeve 200 wherein surgical blade 100 extends a first distance from outer sleeve distal end 201 and blade 120 has a first exposed blade width. Illustratively, distal detent 221 may be configured to temporarily fix surgical blade 100 in a second position relative to outer sleeve 200 wherein surgical blade 100 extends a second distance from outer sleeve distal end 201 and blade 120 has a second exposed blade width. In one or more embodiments, the second exposed blade width may be greater than the first exposed blade width. For example, a surgeon or a surgeon's assistant may selectively actuate surgical blade 100 from a first position relative to outer sleeve 200 to a second position relative to outer sleeve 200. Illustratively, while temporarily fixed in the first position relative to outer sleeve 200, surgical blade 100 may be configured to make a surgical incision, e.g., of a first width, and while temporarily fixed in the second position relative to outer sleeve 200, surgical blade 100 may be configured to make a surgical incision, e.g., of a second width.

In one or more embodiments, pressure mechanism 420 may be configured to provide a variable resistive force to resist an actuation of actuation pin 230. For example, pressure mechanism 420 may be configured to provide a first resistive force with a first magnitude to resist an actuation of actuation pin 230 when actuation pin 230 is in a first position relative to outer sleeve 200. Illustratively, pressure mechanism 420 may be configured to provide a second resistive force with a second magnitude to resist an actuation of actuation pin 230 when actuation pin 230 is in a second position relative to outer sleeve 200.

In one or more embodiments, pressure mechanism 420 may be configured to provide a first resistive force with a first magnitude that resists an egress 710 of actuation pin 230 out of proximal detent 222. Illustratively, pressure mechanism 420 may be configured to provide a second resistive force with a second magnitude that resists an actuation 730 of actuation pin 230 along actuation channel 225. In one or more embodiments, the first magnitude of the first resistive force may not be identical to the second magnitude of the second resistive force. For example, the second magnitude of the second resistive force may be greater than the first magnitude of the first resistive force.

Illustratively, pressure mechanism 420 may be configured to provide a variable resistive force to resist an actuation of actuation pin 230 along actuation channel 225 wherein the magnitude of the variable resistive force increases as actuation pin 230 is actuated from actuation channel proximal end 227 towards actuation channel distal end 226. In one or more embodiments, pressure mechanism 420 may be configured to provide a variable resistive force to resist an actuation of actuation pin 230 wherein the variable resistive force has a maximum magnitude when actuation pin 230 is located at actuation channel distal end 226. For example, pressure mechanism 420 may be configured to provide a small resistive force to resist an egress 710 of actuation pin 230 from proximal detent 222 and a large resistive force to resist an egress 810 of actuation pin 230 from distal detent 221. Illustratively, pressure mechanism 420 may be configured to allow a surgeon or a surgeon's assistant to initiate an actuation of surgical blade 100 from a safe position 500 to a surgical position 600 with a smaller force magnitude, e.g., applied to actuation control apparatus 350, than a force magnitude that may be required to initiate an actuation of surgical blade 100 from a surgical position 600 to a safe position 500.

Figure 9A:
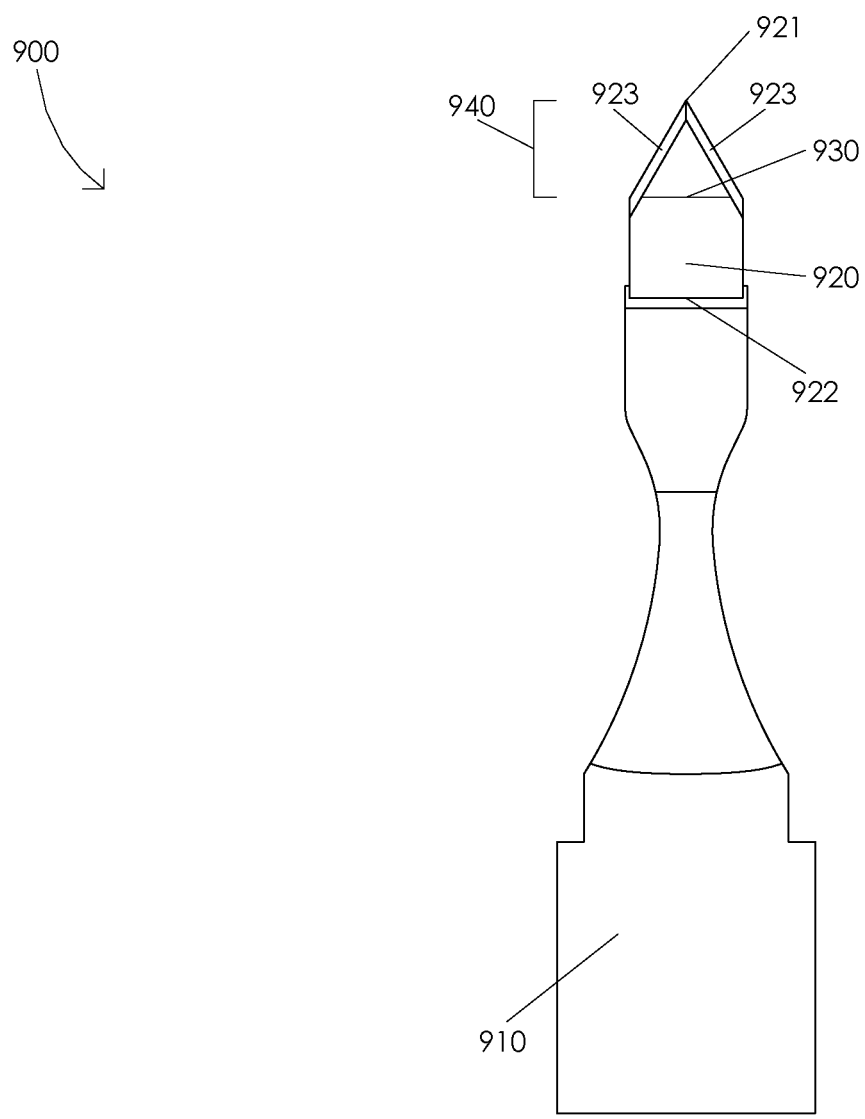
FIGS. 9A, 9B, and 9C are schematic diagrams illustrating a surgical blade.

FIG. 9A is a schematic diagram illustrating a surgical blade 900. In one or more embodiments, surgical blade 900 may comprise a blade mount 910 and a blade 920. Illustratively, blade mount 910 may be configured to support blade 920. Blade mount 910 may be manufactured from any suitable material, e.g., polymers, metals, metal alloys, etc., or from any combination of suitable materials. Illustratively, blade 920 may be configured to make surgical incisions. Blade 920 comprises a blade distal end 921, a blade proximal end 922, and at least one blade edge 923. Blade 920 may be manufactured from any suitable material, e.g., sapphire, diamond, silicon, polymers, metals, metal alloys, etc., or from any combination of suitable materials.

In one or more embodiments, surgical blade 900 may comprise a surgical incision guide 930. Illustratively, surgical incision guide 930 may be configured to provide information, e.g., information about a surgical incision. For example, surgical incision guide 930 may be located at a specific distance 940 from blade distal end 921. Illustratively, a surgeon may compare a location of an outer surface of a tissue with a location of surgical incision guide 930 during a surgical incision, e.g., to provide information about the surgical incision. For example, surgical incision guide 930 may be configured to indicate a surgical incision depth of blade 920 in a tissue. In one or more embodiments, surgical incision guide 930 may be configured to indicate a desired surgical incision depth, e.g., to inform a surgeon that blade 920 is penetrating a tissue at a desirable depth. Illustratively, surgical incision guide 930 may be configured to indicate an undesirable surgical incision depth, e.g., to inform a surgeon that blade 920 is penetrating a tissue at an undesirable depth.

In one or more embodiments, surgical incision guide 930 may be configured to guide a multi-plane surgical incision. A surgeon may perform a multi-plane incision by initially penetrating a tissue to a first depth with blade 920 oriented at a first angle relative to the tissue and then penetrating the tissue to a second depth with blade 920 oriented at a second angle relative to the tissue. Illustratively, surgical incision guide 930 may be configured to indicate that blade 920 is at an optimal depth within a tissue, e.g., by a comparison of an outer surface of the tissue with a location of surgical incision guide 930, for a surgeon to change surgical incision planes within the tissue.

For example, when a surgeon is performing a multi-plane surgical incision, surgical incision guide 930 may be configured to guide the surgeon to penetrate blade 920 to a first depth in a tissue wherein blade 920 may be orientated at a first angle relative to a plane normal to a portion of the surface of the tissue. After penetrating blade 920 to the first depth in the tissue at the first angle relative to the plane normal to the portion of the surface of the tissue, the surgeon may adjust an orientation of blade 920 to a second angle relative to the plane normal to the portion of the surface of the tissue, and then the surgeon may penetrate blade 920 to a second depth in the tissue.

Illustratively, surgical incision guide 930 may comprise a visual signal configured to differentiate a first portion of blade 920 from a second portion of blade 920. For example, surgical incision guide 930 may comprise a marking, e.g., a line, on the surface of blade 920. Illustratively, surgical incision guide 930 may comprise a biocompatible paint or ink. Surgical incision guide 930 may be manufactured by any suitable means for marking a portion of blade 920. In one or more embodiments, surgical incision guide 930 may be manufactured by etching, e.g., laser etching, a marking on blade 920. Illustratively, surgical incision guide 930 may be configured to minimize friction, e.g., between blade 920 and a tissue during a surgical procedure. For example, surgical incision guide 930 may be configured to minimize variation in a geometry of a portion of blade 920.

In one or more embodiments, blade 920 may comprise information about blade 920. Illustratively, one or more dimensions of blade 920 may be marked on blade 920, e.g., by laser etching or by biocompatible paint or ink, or by any other suitable means. For example, a blade 920 with a width of, e.g., 2.0 mm, may have the numbers and distance units "2.0 mm" marked on a portion of blade 920. Illustratively, a blade 920 with a width of, e.g., 2.0 mm, may have the numbers "2.0" or the number "2" marked on a portion of blade 920.

In one or more embodiments, blade 920 may comprise information about a location of surgical incision guide 930 on blade 920. Illustratively, information about a location of surgical incision guide 930 may be marked on blade 920, e.g., by laser etching or by biocompatible paint or ink, or by any other suitable means. For example, a distance between a location of surgical incision guide 930 and blade distal end 921 may be marked on a portion of blade 920. Illustratively, if a distance between surgical incision guide 930 and blade distal end 921 is, e.g., 0.25 mm, the numbers and the distance units "0.25 mm" may be marked on a portion of blade 920. For example, if a distance between surgical incision guide 930 and blade distal end 921 is, e.g., 0.25 mm, the numbers "0.25" or the number "0.25" may be marked on a portion of blade 920.

Figure 9B:
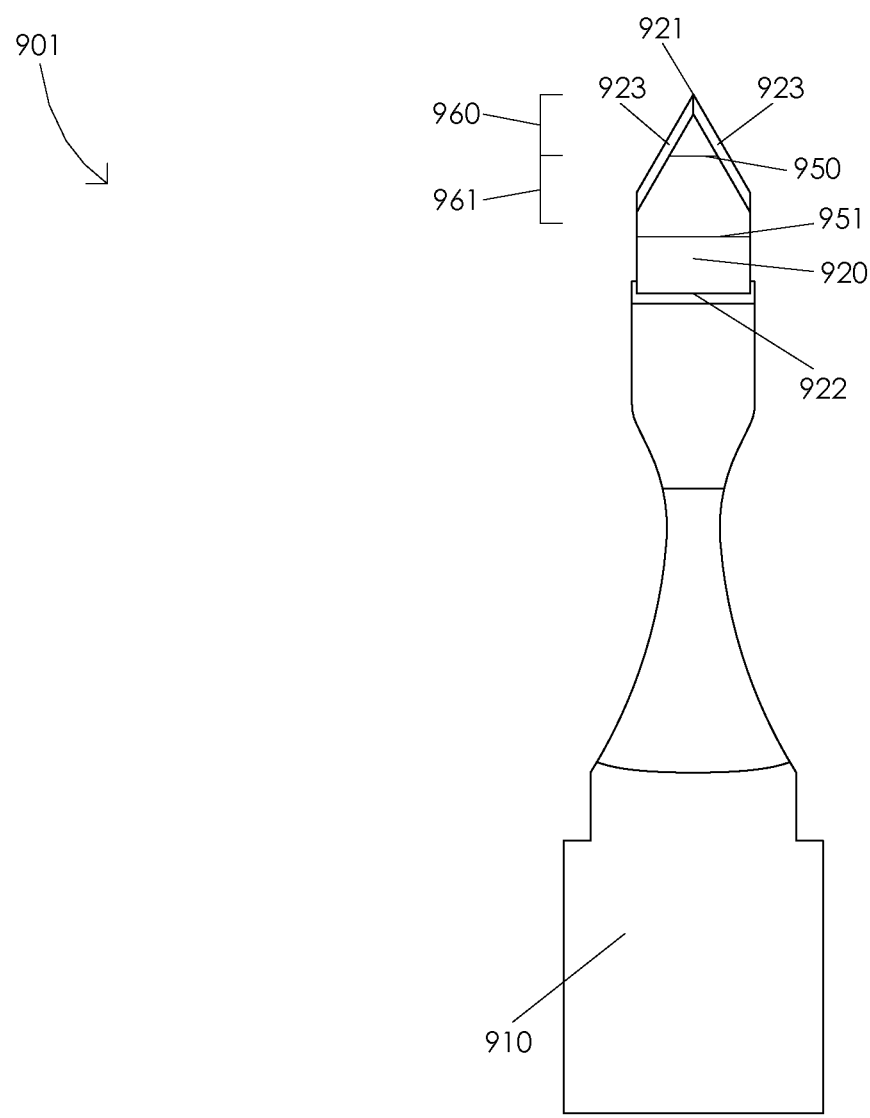

FIG. 9B is a schematic diagram illustrating a surgical blade 901. In one or more embodiments, surgical blade 901 may comprise a first surgical incision guide 950 and a second surgical incision guide 951. Illustratively, first surgical incision guide 950 may be located at a first specific distance 960 from blade distal end 921. In one or more embodiments, second surgical incision guide 951 may be located at a second specific distance 961 from first surgical incision guide 950.

Illustratively, first surgical incision guide 950 and second surgical incision guide 951 may be configured to provide information, e.g., information about a surgical incision. For example, first surgical incision guide 950 and second surgical incision guide 951 may be configured to indicate a safe or desirable range of surgical penetration depths. Illustratively, a surgeon may need to penetrate blade 920 at least a required depth in a particular tissue, but also need to not penetrate blade 920 more than an undesirable depth in the particular tissue. In one or more embodiments, first surgical incision guide 950 may be configured to indicate a required surgical penetration depth and second surgical incision guide 951 may be configured to indicate an undesirable surgical penetration depth in a particular tissue.

In one or more embodiments, first surgical incision guide 950 and second surgical incision guide 951 may be configured to guide a multi-plane surgical incision. Illustratively, first surgical incision guide 950 may be configured to indicate that blade 920 is at a first optimal depth within a tissue, e.g., by a comparison of an outer surface of the tissue with a location of first surgical incision guide 950, for a surgeon to change surgical incision planes within the tissue. In one or more embodiments, second surgical incision guide 951 may be configured to indicate that blade 920 is at a second optimal depth within a tissue for the surgeon to change surgical incision planes within the tissue.

For example, when a surgeon is performing a multi-plane surgical incision, first surgical incision guide 950 may be configured to guide the surgeon to penetrate blade 920 to a first depth in a tissue wherein blade 920 may be orientated at a first angle relative to a plane normal to a portion of the surface of the tissue. After penetrating blade 920 to the first depth in the tissue at the first angle relative to the plane normal to the portion of the surface of the tissue, the surgeon may adjust an orientation of blade 920 to a second angle relative to the plane normal to the portion of the surface of the tissue, and then the surgeon may penetrate blade 920 to a second depth in the tissue. Illustratively, second surgical incision guide 951 may be configured to guide the surgeon to penetrate blade 920 to a second depth in the tissue wherein blade 920 may be oriented at a second angle relative to the plane normal to the portion of the surface of the tissue. After penetrating blade 920 to the second depth in the tissue at the second angle relative to the plane normal to the portion of the surface of the tissue, the surgeon may adjust an orientation of blade 920 to a third angle relative to the plane normal to the portion of the surface of the tissue, and then the surgeon may penetrate blade 920 to a third depth in the tissue.

Figure 9C:
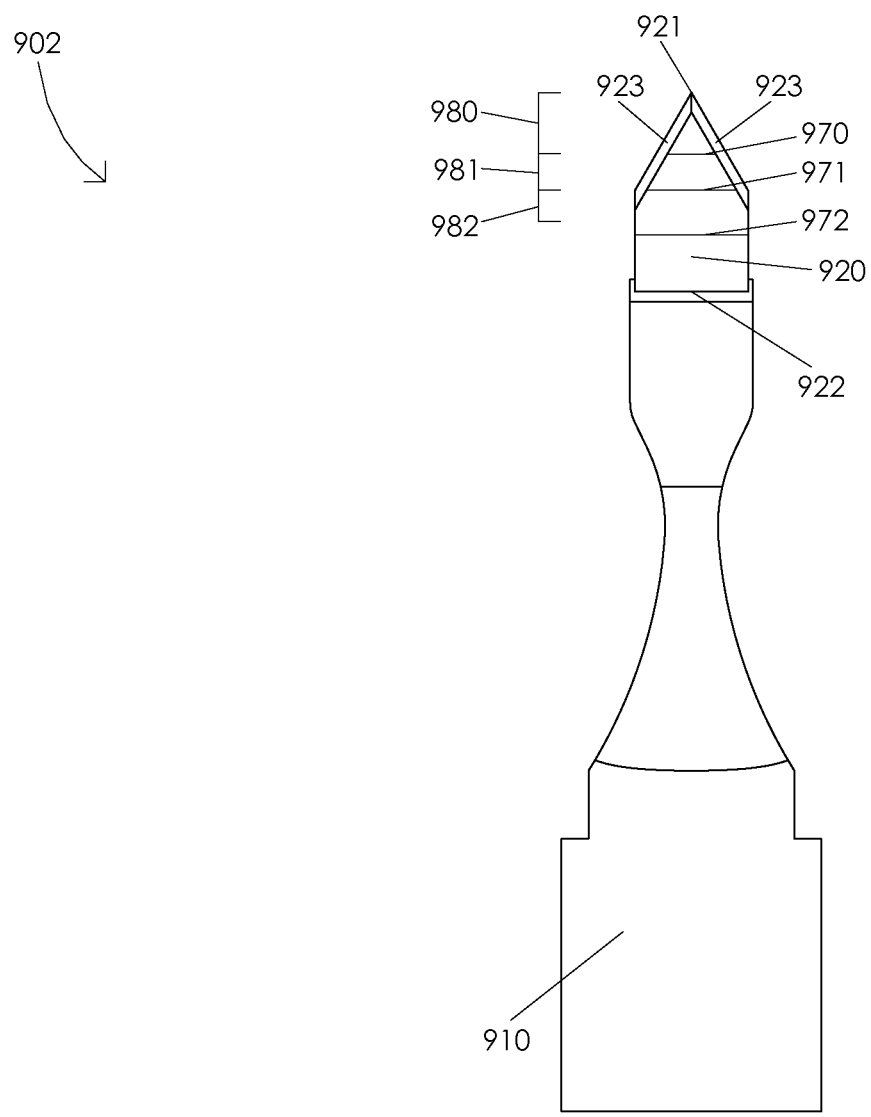

FIG. 9C is a schematic diagram illustrating a surgical blade 902. In one or more embodiments, surgical blade 902 may comprise a first surgical incision guide 970, a second surgical incision guide 971, and a third surgical incision guide 972. Illustratively, first surgical incision guide 970 may be located at a first specific distance 980 from blade distal end 921. In one or more embodiments, second surgical incision guide 971 may be located at a second specific distance 981 from first surgical incision guide 970. Illustratively, third surgical incision guide 972 may be located at a third specific distance 982 from second surgical incision guide 971.

In one or more embodiments, first surgical incision guide 970, second surgical incision guide 971, and third surgical incision guide 972 may be configured to guide a multi-plane surgical incision. Illustratively, first surgical incision guide 970 may be configured to indicate that blade 920 is at a first optimal depth within a tissue, e.g., by a comparison of an outer surface of the tissue with a location of first surgical incision guide 970, for a surgeon to change surgical incision planes within the tissue. In one or more embodiments, second surgical incision guide 971 may be configured to indicate that blade 920 is at a second optimal depth within a tissue for the surgeon to change surgical incision planes within the tissue. Illustratively, third surgical incision guide 972 may be configured to indicate that blade 920 is at a third optimal depth within a tissue for the surgeon to change surgical incision planes within the tissue.

For example, when a surgeon is performing a multi-plane surgical incision, first surgical incision guide 970 may be configured to guide the surgeon to penetrate blade 920 to a first depth in a tissue wherein blade 920 may be orientated at a first angle relative to a plane normal to a portion of the surface of the tissue. After penetrating blade 920 to the first depth in the tissue at the first angle relative to the plane normal to the portion of the surface of the tissue, the surgeon may adjust an orientation of blade 920 to a second angle relative to the plane normal to the portion of the surface of the tissue, and then the surgeon may penetrate blade 920 to a second depth in the tissue. Illustratively, second surgical incision guide 971 may be configured to guide the surgeon to penetrate blade 920 to a second depth in the tissue wherein blade 920 may be oriented at a second angle relative to the plane normal to the portion of the surface of the tissue. After penetrating blade 920 to the second depth in the tissue at the second angle relative to the plane normal to the portion of the surface of the tissue, the surgeon may adjust an orientation of blade 920 to a third angle relative to the plane normal to the portion of the surface of the tissue, and then the surgeon may penetrate blade 920 to a third depth in the tissue. Illustratively, third surgical incision guide 972 may be configured to guide the surgeon to penetrate blade 920 to a third depth in the tissue wherein blade 920 may be oriented at a third angle relative to the plane normal to the portion of the surface of the tissue. After penetrating blade 920 to the third depth in the tissue at the third angle relative to the plane normal to the portion of the surface of the tissue, the surgeon may adjust an orientation of blade 920 to a fourth angle relative to the plane normal to the portion of the surface of the tissue, and then the surgeon may penetrate blade 920 to a fourth depth in the tissue.

Figure 10A:
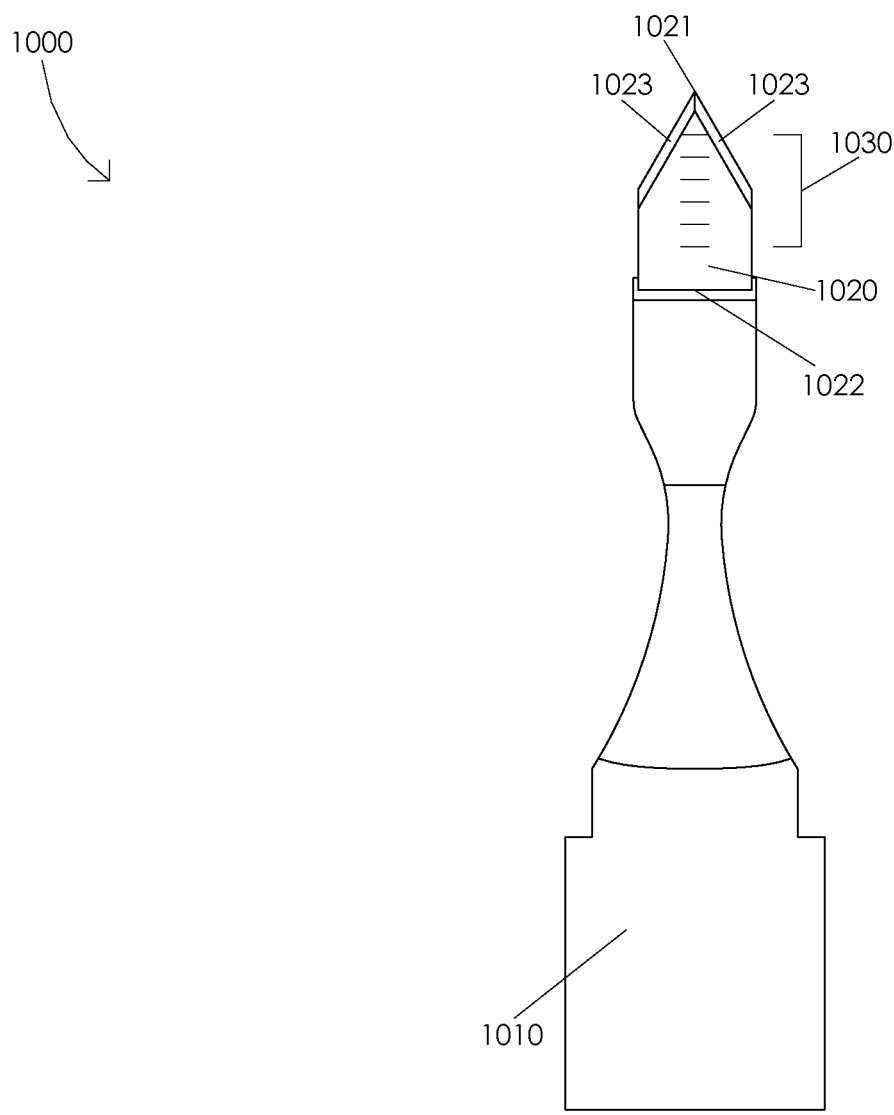
FIGS. 10A and 10B are schematic diagrams illustrating a surgical blade.

FIG. 10A is a schematic diagram illustrating a surgical blade 1000. In one or more embodiments, surgical blade 1000 may comprise a blade mount 1010 and a blade 1020. Illustratively, blade mount 1010 may be configured to support blade 1020. Blade mount 1010 may be manufactured from any suitable material, e.g., polymers, metals, metal alloys, etc., or from any combination of suitable materials. Illustratively, blade 1020 may be configured to make surgical incisions. Blade 1020 comprises a blade distal end 1021, a blade proximal end 1022, and at least one blade edge 1023. Blade 1020 may be manufactured from any suitable material, e.g., sapphire, diamond, silicon, polymers, metals, metal alloys, etc., or from any combination of suitable materials.

In one or more embodiments, surgical blade 1000 may comprise a universal surgical incision guide 1030. Illustratively, universal surgical incision guide 1030 may comprise a plurality of surgical guide marks configured to provide information, e.g., information about a surgical incision. For example, a plurality of surgical guide marks of universal surgical incision guide 1030 may be located on blade 1020 at discrete distances from blade distal end 1021 and the plurality of surgical guide marks of universal surgical incision guide 1030 may be configured to indicate a surgical incision depth in a tissue. Illustratively, a first surgical guide mark of universal surgical incision guide 1030 may be located, e.g., 0.5 mm from blade distal end 1021; a second surgical guide mark of universal surgical incision guide 1030 may be located, e.g., 1.0 mm from blade distal end 1021; a third surgical guide mark of universal surgical incision guide 1030 may be located, e.g., 1.5 mm from blade distal end 1021; a fourth surgical guide mark of universal surgical incision guide 1030 may be located, e.g., 2.0 mm from blade distal end 1021, etc. In one or more embodiments, universal surgical incision guide 1030 may be configured to guide a multi-plane surgical incision. For example, one or more surgical guide marks of universal surgical incision guide 1030 may be configured to indicate an optimal depth within a tissue for a surgeon to adjust a surgical incision plane within the tissue. Illustratively, universal surgical incision guide 1030 may be configured to train a surgeon, e.g., to correctly perform a multi-plane surgical incision.

In one or more embodiments, blade 1020 may comprise information about blade 1020. Illustratively, one or more dimensions of blade 1020 may be marked on blade 1020, e.g., by laser etching or by biocompatible paint or ink, or by any other suitable means. For example, a blade 1020 with a width of, e.g., 2.0 mm, may have the numbers and distance units "2.0 mm" marked on a portion of blade 1020. Illustratively, a blade 1020 with a width of, e.g., 2.0 mm, may have the numbers "2.0" or the number "2" marked on a portion of blade 1020.

In one or more embodiments, blade 1020 may comprise information about a location of one or more surgical guide marks of surgical incision guide 1030 on blade 1020. Illustratively, information about a location of one or more surgical guide marks of surgical incision guide 1030 may be marked on blade 1020, e.g., by laser etching or by biocompatible paint or ink, or by any other suitable means. For example, a distance between a location of one or more surgical guide marks of surgical incision guide 1030 and blade distal end 1021 may be marked on a portion of blade 1020.

In one or more embodiments, if a distance between a first surgical guide mark of surgical incision guide 1030 and blade distal end 1021 is, e.g., 0.5 mm, the numbers and the distance units "0.5 mm" may be marked on a portion of blade 1020. For example, if a distance between a first surgical guide mark of surgical incision guide 1030 and blade distal end 1021 is, e.g., 0.5 mm, the numbers "0.5" or the number "0.5" may be marked on a portion of blade 1020. Illustratively, if a distance between a second surgical guide mark of surgical incision guide 1030 and blade distal end 1021 is, e.g., 1.0 mm, the numbers and the distance units "1.0 mm" may be marked on a portion of blade 1020. For example, if a distance between a second surgical guide mark of surgical incision guide 1030 and blade distal end 1021 is, e.g., 1.0 mm, the numbers "1.0" or the number "1" may be marked on a portion of blade 1020.

Figure 10B:
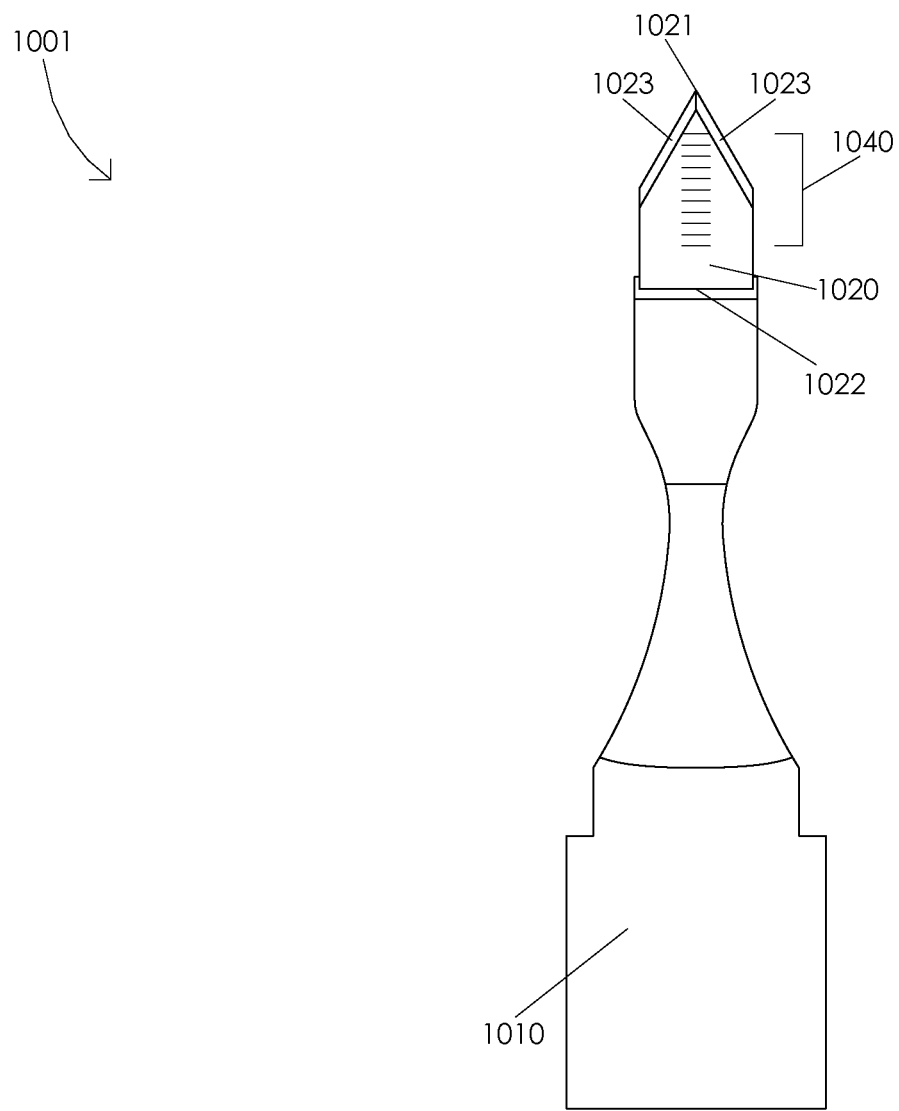

FIG. 10B is a schematic diagram illustrating a surgical blade 1001. In one or more embodiments, surgical blade 1001 may comprise a universal surgical incision guide 1040. Illustratively, universal surgical incision guide 1040 may comprise a plurality of surgical guide marks configured to provide information, e.g., information about a surgical incision. For example, a plurality of surgical guide marks of universal surgical incision guide 1040 may be located on blade 1020 at discrete distances from blade distal end 1021 and the plurality of surgical guide marks of universal surgical incision guide 1040 may be configured to indicate a surgical incision depth in a tissue. Illustratively, a first surgical guide mark of universal surgical incision guide 1040 may be located, e.g., 0.25 mm from blade distal end 1021; a second surgical guide mark of universal surgical incision guide 1040 may be located, e.g., 0.5 mm from blade distal end 1021; a third surgical guide mark of universal surgical incision guide 1040 may be located, e.g., 0.75 mm from blade distal end 1021; a fourth surgical guide mark of universal surgical incision guide 1040 may be located, e.g., 1.0 mm from blade distal end 1021, etc. In one or more embodiments, universal surgical incision guide 1040 may be configured to guide a multi-plane surgical incision. For example, one or more surgical guide marks of universal surgical incision guide 1040 may be configured to indicate an optimal depth within a tissue for a surgeon to adjust a surgical incision plane within the tissue.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any instrument regardless of the instrument's purpose or use. Furthermore, while this description has been written in terms of an ophthalmic surgical blade, the teachings of the present invention are equally suitable to any instrument where the functionality of the invention may be employed. Therefore, it is the object of the appended claims to cover all such variations and modifications as come within the true spirit and scope of the invention.

What is claimed is:

1. A method comprising:

fixing a blade of an ophthalmic surgical instrument in a first position relative to an outer sleeve of the ophthalmic surgical instrument wherein the blade is disposed in a blade mount and wherein the blade mount is fixed to an inner handle of the ophthalmic surgical instrument, the inner handle having a pressure mechanism foundation, a distal outer sleeve interface, a proximal outer sleeve interface, an inner handle base, and an actuation control apparatus;

indicating a property of the blade to a surgeon by a blade indication signal of the actuation control apparatus;

increasing a total contact area between the surgeon's finger tips and the outer sleeve of the ophthalmic surgical instrument by a plurality of grip points of the outer sleeve wherein the outer sleeve has an actuation pin access port, an outer sleeve proximal core, an outer sleeve distal core, and a pressure mechanism distal interface;

providing a first resistive force to resist an actuation of an actuation pin of the ophthalmic surgical instrument out from a proximal detent of the outer sleeve wherein the first resistive force is provided by a spring and wherein the spring has a spring constant-of less than 0.01 N/mm;

actuating the actuation pin of the ophthalmic surgical instrument out from the proximal detent of the outer sleeve;

rotating the inner handle of the ophthalmic surgical instrument in a first direction relative to the outer sleeve;

actuating the actuation pin into an actuation channel of the outer sleeve;

providing a second resistive force to resist an actuation of the actuation pin along the actuation channel wherein the second resistive force is provided by the spring;

actuating the actuation pin along the actuation channel;

aligning the actuation pin for an ingress into an intermediate detent of the outer sleeve;

rotating the inner handle in a second direction relative to the outer sleeve;

providing a first facilitating force to facilitate an actuation of the actuation pin into the intermediate detent wherein the first facilitating force is provided by the spring;

actuating the actuation pin into the intermediate detent;

fixing the blade in a second position relative to the outer sleeve wherein the blade extends a first distance from a distal end of the outer sleeve and wherein the blade has a first exposed blade width;

preventing unintentional movement of the blade during a surgical procedure;

positioning the blade at a first angle relative to a plane normal to a portion of a surface of a tissue;

penetrating the tissue with the blade positioned at the first angle relative to the plane normal to the portion of the surface of the tissue wherein the blade is configured to make a first surgical incision of the first exposed blade width;

identifying a first surgical incision depth by comparing the portion of the surface of the tissue to a first surgical incision guide of the blade wherein the first surgical incision guide of the blade is located 0.25 millimeters from a distal end of the blade;

positioning the blade at a second angle relative to the plane normal to the portion of the surface of the tissue to increase a total surface area of the tissue severed by the blade;

providing a third resistive force to resist an actuation of the actuation pin out from the intermediate detent wherein the third resistive force is provided by the spring;

actuating the actuation pin out from the intermediate detent;

aligning the actuation pin for an ingress into a distal detent of the outer sleeve;

providing a second facilitating force to facilitate an actuation of the actuation pin into the distal detent wherein the second facilitating force is provided by the spring;

actuating the actuation pin into the distal detent; and fixing the blade in a third position relative to the outer sleeve wherein the blade extends a second distance from the distal end of the outer sleeve and wherein the blade has a second exposed blade width.

2. The method of claim 1 further comprising:

penetrating the tissue with the blade positioned at the second angle relative to the plane normal to the portion of the surface of the tissue.

3. The method of claim 2 further comprising:

identifying a second surgical incision depth by comparing the portion of the surface of the tissue to a second surgical incision guide of the blade.

4. The method of claim 2 wherein the blade is configured to make a second surgical incision of the second exposed blade width.

5. The method of claim 4 wherein the second exposed blade width is greater than the first exposed blade width.

6. The method of claim 3 further comprising:

positioning the blade at a third angle relative to the plane normal to the portion of the surface of the tissue wherein the third angle is different from the second angle.

7. The method of claim 6 further comprising:

penetrating the tissue with the blade positioned at the third angle relative to the plane normal to the portion of the surface of the tissue.

8. The method of claim 1 wherein the blade is manufactured from sapphire.

9. The method of claim 1 wherein the first surgical incision guide is laser etched into the blade.

10. The method of claim 1 further comprising:

grasping the actuation control apparatus of the ophthalmic surgical instrument; and rotating the inner handle of the ophthalmic surgical instrument relative to the outer sleeve.

11. A method comprising:

fixing a blade of an ophthalmic surgical instrument in a first position relative to an outer sleeve of the ophthalmic surgical instrument wherein the blade is disposed in a blade mount and wherein the blade mount is fixed to an inner handle of the ophthalmic surgical instrument, the inner handle having a pressure mechanism foundation, a distal outer sleeve interface, a proximal outer sleeve interface, an inner handle base, and an actuation control apparatus;

indicating a property of the blade to a surgeon by a blade indication signal of the actuation control apparatus;

increasing a total contact area between the surgeon's finger tips and the outer sleeve of the ophthalmic surgical instrument by a plurality of grip points of the outer sleeve wherein the outer sleeve has an actuation pin access port, an outer sleeve proximal core, an outer sleeve distal core, and a pressure mechanism distal interface;

providing a first resistive force to resist an actuation of an actuation pin of the ophthalmic surgical instrument out from a proximal detent of the outer sleeve wherein the first resistive force is provided by a spring and wherein the spring has a spring constant of less than 0.01 N/mm;

actuating the actuation pin of the ophthalmic surgical instrument out from the proximal detent of the outer sleeve;

rotating the inner handle of the ophthalmic surgical instrument in a first direction relative to the outer sleeve;

actuating the actuation pin into an actuation channel of the outer sleeve;

providing a second resistive force to resist an actuation of the actuation pin along the actuation channel wherein the second resistive force is provided by the spring;

actuating the actuation pin along the actuation channel;

aligning the actuation pin for an ingress into an intermediate detent of the outer sleeve;

rotating the inner handle in a second direction relative to the outer sleeve;

providing a first facilitating force to facilitate an actuation of the actuation pin into the intermediate detent wherein the first facilitating force is provided by the spring;

actuating the actuation pin into the intermediate detent;

fixing the blade in a second position relative to the outer sleeve wherein the blade extends a first distance from a distal end of the outer sleeve and wherein the blade has a first exposed blade width;

preventing unintentional movement of the blade during a surgical procedure;

positioning the blade at a first angle relative to a plane normal to a portion of a surface of a corneal tissue;

penetrating the corneal tissue to a first penetration depth with the blade positioned at the first angle relative to the plane normal to the portion of the surface of the corneal tissue wherein the blade is configured to make a first surgical incision of the first exposed blade width;

comparing the surface of the corneal tissue to a first minimum guide mark of the blade wherein the first minimum guide mark of the blade is located 0.25 millimeters from a distal end of the blade;

comparing the surface of the corneal tissue to a first maximum guide mark of the blade wherein the first maximum guide mark of the blade is located 0.5 millimeters from the distal end of the blade;

positioning the blade at a second angle relative to the plane normal to the portion of the surface of the corneal tissue to increase a total surface area of the corneal tissue severed by the blade;

providing a third resistive force to resist an actuation of the actuation pin out from the intermediate detent wherein the third resistive force is provided by the spring;

actuating the actuation pin out from the intermediate detent;

aligning the actuation pin for an ingress into a distal detent of the outer sleeve;

providing a second facilitating force to facilitate an actuation of the actuation pin into the distal detent wherein the second facilitating force is provided by the spring;

actuating the actuation pin into the distal detent; and fixing the blade in a third position relative to the outer sleeve wherein the blade extends a second distance from the distal end of the outer sleeve and wherein the blade has a second exposed blade width.

12. The method of claim 11 further comprising:

penetrating the corneal tissue to a second penetration depth with the blade positioned at the second angle relative to the plane normal to the portion of the surface of the corneal tissue.

13. The method of claim 12 further comprising:

ensuring that the second penetration depth is greater than 0.25 millimeters and less than 0.5 millimeters.

14. The method of claim 12 wherein the blade is configured to make a second surgical incision of the second exposed blade width.

15. The method of claim 14 wherein the second exposed blade width is greater than the first exposed blade width.

16. The method of claim 13 further comprising:

comparing the surface of the corneal tissue to a second minimum guide mark of the blade; and comparing the surface of the corneal tissue to a second maximum guide mark of the blade.

17. The method of claim 13 further comprising:

positioning the blade at a third angle relative to the plane normal to the portion of the surface of the corneal tissue wherein the third angle is different from the second angle.

18. The method of claim 17 further comprising:

penetrating the corneal tissue to a third penetration depth with the blade at the third angle relative to the plane normal to the portion of the surface of the corneal tissue.

19. The method of claim 11 wherein the first minimum guide mark is laser etched into the blade and wherein the first maximum guide mark is laser etched into the blade.

20. The method of claim 11 further comprising:

grasping the actuation control apparatus of the ophthalmic surgical instrument; and rotating the inner handle of the ophthalmic surgical instrument relative to the outer sleeve.

* * * * *